(12) United States Patent
Kramer et al.

(10) Patent No.: US 12,331,133 B2
(45) Date of Patent: Jun. 17, 2025

(54) THERAPEUTIC ANTIBODIES FOR TREATING LUNG CANCER

(71) Applicant: VANDERBILT UNIVERSITY, Nashville, TN (US)

(72) Inventors: Kevin J. Kramer, Nashville, TN (US); Ivelin Georgiev, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 925 days.

(21) Appl. No.: 17/600,862

(22) PCT Filed: Apr. 3, 2020

(86) PCT No.: PCT/US2020/026553
§ 371 (c)(1),
(2) Date: Oct. 1, 2021

(87) PCT Pub. No.: WO2020/206233
PCT Pub. Date: Oct. 8, 2020

(65) Prior Publication Data
US 2022/0185911 A1 Jun. 16, 2022

Related U.S. Application Data

(60) Provisional application No. 62/829,503, filed on Apr. 4, 2019.

(51) Int. Cl.
*C07K 16/30* (2006.01)
*A61P 35/00* (2006.01)
*C07K 16/22* (2006.01)

(52) U.S. Cl.
CPC .......... *C07K 16/3023* (2013.01); *A61P 35/00* (2018.01); *C07K 16/22* (2013.01); *C07K 16/3092* (2013.01); *C07K 2317/24* (2013.01); *C07K 2317/565* (2013.01)

(58) Field of Classification Search
CPC ............................ C07K 16/3023; C07K 16/22; C07K 16/3092; C07K 2317/24; C07K 2317/565; A61P 35/00
See application file for complete search history.

(56) References Cited

U.S. PATENT DOCUMENTS

| | | | |
|---|---|---|---|
| 4,342,566 A | 8/1982 | Dixon et al. | |
| 5,804,440 A | 9/1998 | Barbas et al. | |
| 6,096,441 A | 8/2000 | Hauser et al. | |
| 10,640,565 B2* | 5/2020 | Back | A61P 1/04 |
| 10,851,144 B2* | 12/2020 | Butz | A61P 17/06 |
| 2009/0155238 A1 | 6/2009 | Weiner et al. | |
| 2014/0099320 A1 | 4/2014 | Throsby et al. | |

FOREIGN PATENT DOCUMENTS

| | | |
|---|---|---|
| WO | 94/04678 | 3/1994 |
| WO | 94/29348 | 12/1994 |
| WO | 2019/143884 | 7/2019 |
| WO | 2020/033164 | 2/2020 |

OTHER PUBLICATIONS

Winkler et al. (Journal of Immunology (2000) 165(8): 4505-4514) (Year: 2000).*
Honegger and Pluckthun. Journal of Molecular Biology (2001) 309(3): 657-670. (Year: 2001).*
Lee et al., 2011, Nature Reviews Cancer 11: 211-218 (Year: 2011).*
Sela-Culang et al. (Frontiers in Immunology (2013) 4: 302) (Year: 2013).*
Almagro et al. Frontiers in Immunology (2018) 8: 1751 (Year: 2018).*
PDQ® Screening and Prevention Editorial Board. PDQ Cancer Prevention Overview. Bethesda, MD: National Cancer Institute. Updated Oct. 23, 2023. Available at: https://www.cancer.gov/about-cancer/causes-prevention/patient-prevention-overview-pdq. Accessed Mar. 22, 2024. [PMID: 26389424] (Year: 2023).*
Extended European Search Report for EP Application No. 20784505.8 dated Jan. 24, 2023, 13 pages.
McDaniel et al., "Identification of tumor-reactive B cells and systemic IgG in breast cancer based on clonal frequency in the sentinel lympyh node" Immunotherapy, Jan. 1, 2018, pp. 729-738.
Bondgaard et al., "High specificity but low sensitivity of mutation-specific antibodies against EGFR mutations in non-small-cell lung cancer", Modern Pathology, vol. 27, No. 12, Apr. 25, 2014, pp. 1590-1598.
Wang et al., "Tumor-infiltrating B cells: their role and application in anti-tumor immunity in lung cancer", Cellular & Molecular Immunology, Nature Publishing Group Uk, London, vol. 16, No. 1, Apr. 8, 2018, pp. 6-18.
Muffly et al., "Early results of phase 1 study of JSP191, an anti-CD117 monoclonal antibody, with non-myeloablative conditioning in older adults with MRD-positive MDS/AML undergoing allogeneic hematopoietic cell transplantation", Journal of Clinical Oncology, Jan. 1, 2021, Meeting Abstract, 2021 ASCO Annual Meeting.
Kohler and Milstein, Nature, 256:495 (1975).
Needleman et al. (1970) J. Mol. Biol. 48: 443-453.
Zoller, M.J. Curr. Opin. Biotechnol. 3:348-354, (1992).
Kabat E.A. et al., (1991) Sequences of proteins of immunological interest. NIH Publication 91-3242.
Al-Lazikani et al., 1997. J. Mol. Biol., 273:927-948.
MacCallum et al., 1996, J. Mol. Biol, 262:732-745.
Lefranc et al., Dev. Comp. Immunol., 2003, 27:55-77.
International Preliminary Report on Patentability issued for Application No. PCT/US2020/026553, dated Oct. 14, 2021.

(Continued)

*Primary Examiner* — Brad Duffy
*Assistant Examiner* — Elizabeth A Shupe
(74) *Attorney, Agent, or Firm* — Meunier Carlin & Curfman LLC

(57) ABSTRACT

The present disclosure relates to antibodies and uses thereof for treating lung cancer.

10 Claims, 7 Drawing Sheets

Specification includes a Sequence Listing.

(56) References Cited

OTHER PUBLICATIONS

International Search Report and Written Opinion dated Sep. 1, 2020, from International Application No. PCT/US2020/026553, 11 pages.
Cai, M. et al. "hypothetical protein AS9A_1214 [Hoyosella subflava DQS3-9A1]", Aug. 31, 2017 (online).
McDaniel, Jr et al. "High-throughput discovery of antitumor antibodies mined from sentinel lymph node B cells and circulating IgG of breast cancer patients", Cancer Immunology, Immunotherapy. May 2018, vol. 67, No. 5, pp. 729-738.

* cited by examiner

A

B

A

B

A

B

SEQUENCE LISTING

```
<160> NUMBER OF SEQ ID NOS: 63

<210> SEQ ID NO 1
<211> LENGTH: 8
<212> TYPE: PRT
<213> ORGANISM: Artificial Sequence
<220> FEATURE:
<223> OTHER INFORMATION: Synthetic construct

<400> SEQUENCE: 1

Gly Phe Thr Val Ser Ser Asn Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic construct

<400> SEQUENCE: 2

Ile Tyr Thr Gly Gly Gly Thr
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic construct

<400> SEQUENCE: 3

Ala Arg Glu Ala Pro Phe Thr Ala Ala Leu Tyr Tyr
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Synthetic construct

<400> SEQUENCE: 4

Ser Ser Asp Val Gly
1               5

<210> SEQ ID NO 5

<400> SEQUENCE: 5

000

<210> SEQ ID NO 6
<211> LENGTH: 11
<212> TYPE: PRT
<213> ORGANISM: Artificial Sequence
<220> FEATURE:
<223> OTHER INFORMATION: Synthetic construct
```

<400> SEQUENCE: 6

Ser Ser Tyr Ala Gly Asn Asn Arg Val Val
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic construct

<400> SEQUENCE: 7

Gly Tyr Ile Phe Glu Ala Tyr Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic construct

<400> SEQUENCE: 8

Ile Ser Val Phe Asn Gly Asp Arg
1               5

<210> SEQ ID NO 9
<211> LENGTH: 12
<212> TYPE: PRT
<213> ORGANISM: Artificial Sequence
<220> FEATURE:
<223> OTHER INFORMATION: Synthetic construct

<400> SEQUENCE: 9

Ala Thr Gly Ala Glu Leu Leu Ser Ala Phe Gly Val
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Synthetic construct

<400> SEQUENCE: 10

Thr Ser Asn Ile Gly Ala Gly Tyr Glu
1               5

<210> SEQ ID NO 11

<400> SEQUENCE: 11

000

<210> SEQ ID NO 12
<211> LENGTH: 12
<212> TYPE: PRT
<213> ORGANISM: Artificial Sequence
<220> FEATURE:
<223> OTHER INFORMATION: Synthetic construct

<400> SEQUENCE: 12

Gln Ser Tyr Asp Ser Ser Arg Gly Gly Phe Trp Val
1               5                   10

```
<210> SEQ ID NO 13
<211> LENGTH: 8
<212> TYPE: PRT
<213> ORGANISM: Artificial Sequence
<220> FEATURE:
<223> OTHER INFORMATION: Synthetic construct

<400> SEQUENCE: 13

Gly Phe Ala Phe Ser Thr Tyr Val
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic construct

<400> SEQUENCE: 14

Ile Ser His Glu Gly Ser Asp Lys
1               5

<210> SEQ ID NO 15
<211> LENGTH: 15
<212> TYPE: PRT
<213> ORGANISM: Artificial Sequence
<220> FEATURE:
<223> OTHER INFORMATION: Synthetic construct

<400> SEQUENCE: 15

Ala Lys Glu Gly Pro Arg Asp Tyr Tyr Tyr Gly Trp Asp Val
1               5                   10                  15

<210> SEQ ID NO 16
<211> LENGTH: 9
<212> TYPE: PRT
<213> ORGANISM: Artificial Sequence
<220> FEATURE:
<223> OTHER INFORMATION: Synthetic construct

<400> SEQUENCE: 16

Ser Ser Asp Val Gly Ala Tyr Asn Tyr
1               5

<210> SEQ ID NO 17

<400> SEQUENCE: 17

000

<210> SEQ ID NO 18
<211> LENGTH: 10
<212> TYPE: PRT
<213> ORGANISM: Artificial Sequence
<220> FEATURE:
<223> OTHER INFORMATION: Synthetic construct

<400> SEQUENCE: 18

Ser Ser Tyr Val Arg Ser Gly Thr Arg Val
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic construct
```

```
<400> SEQUENCE: 19

Gly Gly Ser Ile Ser Ser Gly Ser Tyr Tyr
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Synthetic construct

<400> SEQUENCE: 20

Ile Tyr Met Ser Gly Thr Thr
1               5

<210> SEQ ID NO 21
<211> LENGTH: 15
<212> TYPE: PRT
<213> ORGANISM: Artificial Sequence
<220> FEATURE:
<223> OTHER INFORMATION: Synthetic construct

<400> SEQUENCE: 21

Ala Arg Asp Pro Tyr Asn Trp Asn Ala Asn Tyr Tyr Ile Asp Val
1               5                   10                  15

<210> SEQ ID NO 22
<211> LENGTH: 6
<212> TYPE: PRT
<213> ORGANISM: Artificial Sequence
<220> FEATURE:
<223> OTHER INFORMATION: Synthetic construct

<400> SEQUENCE: 22

Gln Gly Ile Arg Asn Asp
1               5

<210> SEQ ID NO 23

<400> SEQUENCE: 23

000

<210> SEQ ID NO 24
<211> LENGTH: 9
<212> TYPE: PRT
<213> ORGANISM: Artificial Sequence
<220> FEATURE:
<223> OTHER INFORMATION: Synthetic construct

<400> SEQUENCE: 24

Leu Gln His Asn Ser Tyr Pro Tyr Thr
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic construct

<400> SEQUENCE: 25

Gly Phe Thr Phe Ser Thr Tyr Val
1               5

<210> SEQ ID NO 26
```

```
<211> LENGTH: 8
<212> TYPE: PRT
<213> ORGANISM: Artificial Sequence
<220> FEATURE:
<223> OTHER INFORMATION: Synthetic construct

<400> SEQUENCE: 26

Ile Trp Tyr Asp Gly Ser Asn Lys
1               5

<210> SEQ ID NO 27
<211> LENGTH: 11
<212> TYPE: PRT
<213> ORGANISM: Artificial Sequence
<220> FEATURE:
<223> OTHER INFORMATION: Synthetic construct

<400> SEQUENCE: 27

Ala Arg Asp Ala Gly Ser Asp Ala Phe Asp Ile
1               5                   10

<210> SEQ ID NO 28
<211> LENGTH: 6
<212> TYPE: PRT
<213> ORGANISM: Artificial Sequence
<220> FEATURE:
<223> OTHER INFORMATION: Synthetic construct

<400> SEQUENCE: 28

Gln Ser Ile Ser Ser Tyr
1               5

<210> SEQ ID NO 29

<400> SEQUENCE: 29

000

<210> SEQ ID NO 30
<211> LENGTH: 9
<212> TYPE: PRT
<213> ORGANISM: Artificial Sequence
<220> FEATURE:
<223> OTHER INFORMATION: Synthetic construct

<400> SEQUENCE: 30

Gln Gln Ser Tyr Ser Thr Pro Ala Thr
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic construct

<400> SEQUENCE: 31

Gly Phe Pro Phe Ser Asn Tyr Trp
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic construct

<400> SEQUENCE: 32
```

```
Ile Ser Gly Asp Gly Ser Ser Thr
1               5

<210> SEQ ID NO 33
<211> LENGTH: 13
<212> TYPE: PRT
<213> ORGANISM: Artificial Sequence
<220> FEATURE:
<223> OTHER INFORMATION: Synthetic construct

<400> SEQUENCE: 33

Ala Arg Val Gln Leu Leu Ala Asp Asp Val Leu Asp Ile
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Synthetic construct

<400> SEQUENCE: 34

Gln Ser Val Tyr Ala Asn His
1               5

<210> SEQ ID NO 35

<400> SEQUENCE: 35

000

<210> SEQ ID NO 36
<211> LENGTH: 9
<212> TYPE: PRT
<213> ORGANISM: Artificial Sequence
<220> FEATURE:
<223> OTHER INFORMATION: Synthetic construct

<400> SEQUENCE: 36

Gln Gln Tyr Gly Arg Ser Pro Leu Thr
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic construct

<400> SEQUENCE: 37

Gly Gly Ile Val His Ser Tyr Ser
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic construct

<400> SEQUENCE: 38

Val Val Pro Val Phe Asp Thr Arg
1               5

<210> SEQ ID NO 39
<211> LENGTH: 22
```

```
<212> TYPE: PRT
<213> ORGANISM: Artificial Sequence
<220> FEATURE:
<223> OTHER INFORMATION: Synthetic construct

<400> SEQUENCE: 39

Gly Arg Leu Thr Tyr His Tyr Asp Ser Ser Gly Phe Val Ser Thr Val
1               5                   10                  15

Gly Asn Ala Leu Asp Val
            20

<210> SEQ ID NO 40
<211> LENGTH: 7
<212> TYPE: PRT
<213> ORGANISM: Artificial Sequence
<220> FEATURE:
<223> OTHER INFORMATION: Synthetic construct

<400> SEQUENCE: 40

Gln Ser Val Thr Asn Ile Tyr
1               5

<210> SEQ ID NO 41

<400> SEQUENCE: 41

000

<210> SEQ ID NO 42
<211> LENGTH: 9
<212> TYPE: PRT
<213> ORGANISM: Artificial Sequence
<220> FEATURE:
<223> OTHER INFORMATION: Synthetic construct

<400> SEQUENCE: 42

His Gln Tyr Gly Ser Ser Pro Gln Thr
1               5

<210> SEQ ID NO 43
<211> LENGTH: 118
<212> TYPE: PRT
<213> ORGANISM: Artificial Sequence
<220> FEATURE:
<223> OTHER INFORMATION: Synthetic construct

<400> SEQUENCE: 43

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Thr Gly Gly Gly Thr Tyr Ala Asp Ser Val Lys
    50                  55                  60

Gly Arg Phe Thr Ile Ser Arg Asp Asn Ser Gln Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Ala Pro Phe Thr Ala Ala Leu Tyr Tyr Trp Gly Gln Gly Thr
            100                 105                 110

Leu Val Thr Val Ser Ser
            115
```

```
<210> SEQ ID NO 44
<211> LENGTH: 111
<212> TYPE: PRT
<213> ORGANISM: Artificial Sequence
<220> FEATURE:
<223> OTHER INFORMATION: Synthetic construct

<400> SEQUENCE: 44
```

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Glu Val Thr Ile Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Asn Arg Val Val Phe Gly Gly Gly Thr Lys Leu Thr Val Leu
            100                 105                 110

```
<210> SEQ ID NO 45
<211> LENGTH: 119
<212> TYPE: PRT
<213> ORGANISM: Artificial Sequence
<220> FEATURE:
<223> OTHER INFORMATION: Synthetic construct

<400> SEQUENCE: 45
```

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Ile Phe Glu Ala Tyr
            20                  25                  30

Gly Ile Asn Trp Ala Arg Gln Ala Pro Gly Gln Gly Leu Glu Trp Leu
        35                  40                  45

Gly Trp Ile Ser Val Phe Asn Gly Asp Arg Gln Tyr Ala Gln Asn Phe
    50                  55                  60

Gln Gly Arg Val Thr Met Thr Thr Asp Lys Ser Ser Asn Thr Ala Tyr
65                  70                  75                  80

Leu Glu Leu Ser Ser Leu Arg Ser Gly Asp Thr Ala Val Tyr Tyr Cys
                85                  90                  95

Ala Thr Gly Ala Glu Leu Leu Ser Ala Phe Gly Val Trp Gly Gln Gly
            100                 105                 110

Thr Thr Val Thr Val Ser Ser
        115

```
<210> SEQ ID NO 46
<211> LENGTH: 112
<212> TYPE: PRT
<213> ORGANISM: Artificial Sequence
<220> FEATURE:
<223> OTHER INFORMATION: Synthetic construct

<400> SEQUENCE: 46
```

Gln Ser Val Leu Thr Gln Pro Pro Ser Val Ser Gly Ala Pro Gly Gln
1               5                   10                  15

```
Arg Val Thr Ile Ser Cys Thr Gly Ser Thr Ser Asn Ile Gly Ala Gly
             20                  25                  30

Tyr Glu Val Asn Trp Tyr Gln Gln Leu Pro Gly Arg Ala Pro Lys Leu
         35                  40                  45

Leu Ile Ser Gly Asn Thr Asp Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Arg Ala Glu Asp Glu Ala Asp Tyr Tyr Cys Gln Ser Tyr Asp Ser Ser
                 85                  90                  95

Arg Gly Gly Phe Trp Val Phe Gly Gly Gly Thr Lys Val Thr Val Leu
            100                 105                 110

<210> SEQ ID NO 47
<211> LENGTH: 122
<212> TYPE: PRT
<213> ORGANISM: Artificial Sequence
<220> FEATURE:
<223> OTHER INFORMATION: Synthetic construct

<400> SEQUENCE: 47

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Thr Tyr
             20                  25                  30

Val Met His Trp Val Arg Gln Ala Pro Gly Lys Gly Leu Glu Trp Val
         35                  40                  45

Ala Ala Ile Ser His Glu Gly Ser Asp Lys Tyr Tyr Val Asp Ser Val
 50                  55                  60

Lys Gly Arg Phe Thr Ile Ser Arg Asp Asn Ser Lys Asn Thr Leu His
 65                  70                  75                  80

Leu Gln Met Asn Ser Leu Arg Ile Glu Asp Thr Ala Val Tyr Tyr Cys
                 85                  90                  95

Ala Lys Glu Gly Pro Arg Asp Tyr Tyr Tyr Gly Trp Asp Val Trp
            100                 105                 110

Gly Gln Gly Thr Thr Val Ile Val Ser Ser
            115                 120

<210> SEQ ID NO 48
<211> LENGTH: 110
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be any naturally occurring amino acid

<400> SEQUENCE: 48

Gln Xaa Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ala Tyr
             20                  25                  30

Asn Tyr Val Ser Trp Tyr Gln Gln Tyr Pro Gly Lys Ala Pro Thr Leu
         35                  40                  45

Leu Ile Phe Glu Val Lys Tyr Arg Pro Ser Gly Val Pro Asn Arg Phe
 50                  55                  60

Ser Gly Ser Lys Ser Gly Asn Thr Ala Ser Leu Thr Ile Ser Gly Leu
```

65                  70                  75                  80

Arg Ser Glu Asp Glu Ala Asp Tyr Tyr Cys Ser Ser Tyr Val Arg Ser
                    85                  90                  95

Gly Thr Arg Val Phe Gly Gly Gly Thr Lys Val Thr Val Leu
                100                 105                 110

<210> SEQ ID NO 49
<211> LENGTH: 123
<212> TYPE: PRT
<213> ORGANISM: Artificial Sequence
<220> FEATURE:
<223> OTHER INFORMATION: Synthetic construct

<400> SEQUENCE: 49

Gln Val Gln Leu Gln Glu Ser Gly Pro Gly Leu Val Lys Pro Ser Gln
1               5                   10                  15

Thr Leu Ser Leu Thr Cys Asn Val Ser Gly Gly Ser Ile Ser Ser Gly
                20                  25                  30

Ser Tyr Tyr Trp Ser Trp Ile Arg Gln Pro Ala Gly Lys Gly Leu Glu
            35                  40                  45

Trp Ile Gly Arg Ile Tyr Met Ser Gly Thr Thr Asn Tyr Asn Pro Ser
        50                  55                  60

Leu Lys Ser Arg Val Thr Ile Ser Leu Asp Thr Ser Lys Asn Gln Phe
65                  70                  75                  80

Ser Leu Arg Leu Arg Ser Val Thr Ala Ala Asp Thr Ala Val Tyr Tyr
                85                  90                  95

Cys Ala Arg Asp Pro Tyr Asn Trp Asn Ala Asn Tyr Tyr Ile Asp Val
                100                 105                 110

Trp Gly Lys Gly Thr Thr Val Thr Val Ser Ser
        115                 120

<210> SEQ ID NO 50
<211> LENGTH: 107
<212> TYPE: PRT
<213> ORGANISM: Artificial Sequence
<220> FEATURE:
<223> OTHER INFORMATION: Synthetic construct

<400> SEQUENCE: 50

Asp Ile Gln Met Thr Gln Ser Pro Ser Ser Leu Ser Ala Phe Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Leu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Leu Gln His Asn Ser Tyr Pro Tyr
                85                  90                  95

Thr Phe Gly Gln Gly Thr Lys Leu Glu Ile Lys
                100                 105

<210> SEQ ID NO 51
<211> LENGTH: 118
<212> TYPE: PRT
<213> ORGANISM: Artificial Sequence
<220> FEATURE:

-continued

<223> OTHER INFORMATION: Synthetic construct

<400> SEQUENCE: 51

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Val Met His Trp Val Arg Gln Ala Pro Gly Lys Gly Leu Glu Trp Val
        35                  40                  45

Ala Val Ile Trp Tyr Asp Gly Ser Asn Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ala Glu Asp Thr Ala Val Tyr Tyr Cys
                85                  90                  95

Ala Arg Asp Ala Gly Ser Asp Ala Phe Asp Ile Trp Gly Gln Gly Thr
            100                 105                 110

Met Val Thr Val Ser Ser
            115

<210> SEQ ID NO 52
<211> LENGTH: 107
<212> TYPE: PRT
<213> ORGANISM: Artificial Sequence
<220> FEATURE:
<223> OTHER INFORMATION: Synthetic construct

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Lys Asp Phe Ala Thr Tyr Tyr Cys Gln Gln Ser Tyr Ser Thr Pro Ala
                85                  90                  95

Thr Phe Gly Gly Gly Thr Lys Val Glu Ile Lys
            100                 105

<210> SEQ ID NO 53
<211> LENGTH: 118
<212> TYPE: PRT
<213> ORGANISM: Artificial Sequence
<220> FEATURE:
<223> OTHER INFORMATION: Synthetic construct

<400> SEQUENCE: 53

Gln Leu Val Glu Ser Gly Gly Ala Ser Val Gln Pro Gly Gly Ser Leu
1               5                   10                  15

Arg Leu Ser Cys Ala Ala Ser Gly Phe Pro Phe Ser Asn Tyr Trp Ile
            20                  25                  30

His Trp Val Arg Gln Ala Pro Gly Lys Gly Pro Glu Trp Val Ser Arg
        35                  40                  45

Ile Ser Gly Asp Gly Ser Ser Thr Ser Tyr Ala Asp Ser Val Lys Gly

```
                 50                  55                  60
Arg Phe Thr Ile Ser Arg Asp Asn Ala Arg Asn Met Leu Tyr Leu Gln
 65                  70                  75                  80

Met Asn Ser Leu Arg Val Glu Asp Thr Ala Leu Tyr Tyr Cys Ala Arg
                 85                  90                  95

Val Gln Leu Leu Ala Asp Asp Val Leu Asp Ile Trp Gly Gln Gly Thr
                100                 105                 110

Met Val Thr Val Ser Ser
            115
```

<210> SEQ ID NO 54
<211> LENGTH: 108
<212> TYPE: PRT
<213> ORGANISM: Artificial Sequence
<220> FEATURE:
<223> OTHER INFORMATION: Synthetic construct

<400> SEQUENCE: 54

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Tyr Ala Asn
                 20                  25                  30

His Ile Ala Trp Tyr Gln Gln Lys Pro Gly Gln Ala Pro Arg Arg Leu
             35                  40                  45

Phe Phe Gly Ala Ser Ile Arg Ala Tyr Gly Ile Pro Asp Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Tyr Gly Arg Ser Pro
                 85                  90                  95

Leu Thr Phe Gly Gly Gly Thr Lys Val Glu Met Lys
            100                 105
```

<210> SEQ ID NO 55
<211> LENGTH: 129
<212> TYPE: PRT
<213> ORGANISM: Artificial Sequence
<220> FEATURE:
<223> OTHER INFORMATION: Synthetic construct

<400> SEQUENCE: 55

```
Gln Val Gln Leu Val Gln Ser Gly Ala Glu Met Lys Lys Pro Gly Ser
 1               5                  10                  15

Ser Val Lys Val Ser Cys Lys Ala Ser Gly Gly Ile Val His Ser Tyr
                 20                  25                  30

Ser Leu Ser Trp Val Arg Gln Ala Pro Gly Gln Gly Leu Glu Trp Val
             35                  40                  45

Gly Gly Val Val Pro Val Phe Asp Thr Arg Lys Tyr Ala Gln Lys Phe
 50                  55                  60

Gln Gly Arg Val Thr Ile Thr Ala Asp Glu Ser Thr Ser Thr Thr Tyr
 65                  70                  75                  80

Met Glu Leu Ser Ser Leu Arg Ser Glu Asp Thr Ala Val Tyr Tyr Cys
                 85                  90                  95

Gly Arg Leu Thr Tyr His Tyr Asp Ser Ser Gly Phe Val Ser Thr Val
            100                 105                 110

Gly Asn Ala Leu Asp Val Trp Gly Gln Gly Thr Met Val Ile Val Ser
            115                 120                 125
```

Ser

```
<210> SEQ ID NO 56
<211> LENGTH: 108
<212> TYPE: PRT
<213> ORGANISM: Artificial Sequence
<220> FEATURE:
<223> OTHER INFORMATION: Synthetic construct

<400> SEQUENCE: 56

Glu Ile Val Leu Met Gln Ser Pro Gly Thr Leu Ser Leu Ser Pro Gly
1               5                   10                  15

Glu Arg Ala Thr Leu Ser Cys Arg Ala Ser Gln Ser Val Thr Asn Ile
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Thr Leu Thr Ile Asn Arg Leu Glu
65                  70                  75                  80

Pro Glu Asp Phe Gly Val Tyr Phe Cys His Gln Tyr Gly Ser Ser Pro
                85                  90                  95

Gln Thr Phe Gly Gln Gly Thr Lys Val Glu Ile Lys
            100                 105

<210> SEQ ID NO 57
<211> LENGTH: 12
<212> TYPE: PRT
<213> ORGANISM: Artificial Sequence
<220> FEATURE:
<223> OTHER INFORMATION: Synthetic construct

<400> SEQUENCE: 57

Ala Arg Val Gln Leu Ala Asp Asp Val Leu Asn Ile
1               5                   10

<210> SEQ ID NO 58
<211> LENGTH: 9
<212> TYPE: PRT
<213> ORGANISM: Artificial Sequence
<220> FEATURE:
<223> OTHER INFORMATION: Synthetic construct

<400> SEQUENCE: 58

Gln Gln Tyr Gly Ser Ser Pro Leu Thr
1               5

<210> SEQ ID NO 59
<211> LENGTH: 14
<212> TYPE: PRT
<213> ORGANISM: Artificial Sequence
<220> FEATURE:
<223> OTHER INFORMATION: Synthetic construct

<400> SEQUENCE: 59

Ala Arg Pro Met Thr Thr Val Thr Pro Lys Ala Phe Asp Ile
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Synthetic construct
```

```
<400> SEQUENCE: 60

Ala Arg Val Gln Leu Leu Ala Asp Asp Val Leu Asp Ile
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Synthetic construct

<400> SEQUENCE: 61

Ala Arg Val Gln Val Leu Ala Asp Asp Val Leu Asn Ile
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic construct

<400> SEQUENCE: 62

Ala Arg Asp Pro Ala Gly Asp Ala Phe Asp Ile
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic construct

<400> SEQUENCE: 63

Ala Arg Asp Pro Ala Trp Gly Ala Tyr Asp Ile
1               5                   10
```

THERAPEUTIC ANTIBODIES FOR TREATING LUNG CANCER

CROSS REFERENCE TO RELATED APPLICATIONS

This application is a United States National Phase Patent Application of International Patent Application Number PCT/US2020/026553, filed on Apr. 3, 2020, which claims the benefit of U.S. Provisional Patent Application Ser. No. 62/829,503 filed Apr. 4, 2019, the disclosures of which are expressly incorporated herein by reference.

REFERENCE TO SEQUENCE LISTING

The Sequence Listing submitted Dec. 27, 2024, as a text file named "10644-094US1_ST25.txt," created on Dec. 16, 2024, and having a size of 24,258 bytes is hereby incorporated by reference pursuant to 37 C.F.R. § 1.824.

FIELD

The present disclosure relates to antibodies and uses thereof for treating lung cancer.

BACKGROUND

Malignancies of the lung are expected to be responsible for over 25% of all cancer-associated mortalities in the United States in 2019. Clinical treatment of lung cancer is complicated by both poor detection of early disease activity and relapse or unresponsiveness to administered therapy. Taken together, these realities of patient outcome underscore the need for alternative therapeutic strategies. Research efforts in the cancer immunology field focus primarily on T cells in the tumor microenvironment, however, there is evidence that B cells may impart a clinical benefit in patients. The formation of tertiary lymphoid structures and antibody secretion in lung tumors associate with positive clinical outcomes yet remain understudied and poorly characterized. What is needed are new compositions and therapeutic antibodies for treating lung cancer.

SUMMARY

Disclosed herein are therapeutic antibodies and methods for treating lung cancer. As described herein, B cells were isolated from human lung cancer tissue and recovered B-cell receptor (BCR) sequences were identified by paired heavy and light chain single cell RNA sequencing. From these experiments, clonally expanded B-cell populations and convergent BCR sequences shared between different patients were identified. The inventors have also demonstrated that the recombinant antibodies described herein bind cultured lung cancer cell lines in a dose-dependent manner. These novel antibodies provide for new and improved therapeutic and diagnostic antibodies.

In some aspects, disclosed herein is a recombinant antibody, wherein the antibody comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH3 comprises an amino acid sequence at least 60% identical to:

| | |
|---|---|
| AREAPFTAALLYY, | (SEQ ID NO: 3) |
| ATGAELLSAFGV, | (SEQ ID NO: 9) |
| AKEGPRDYYYYGWDV, | (SEQ ID NO: 15) |
| ARDPYNWNANYYIDV, | (SEQ ID NO: 21) |
| ARDAGSDAFDI, | (SEQ ID NO: 27) |
| ARVQLLADDVLDI, or | (SEQ ID NO: 33) |
| GRLTYHYDSSGFVSTVGNALDV; | (SEQ ID NO: 39) |

CDRL3 comprises an amino acid sequence at least 60% identical to:

| | |
|---|---|
| SSYAGNNNRVV, | (SEQ ID NO: 6) |
| QSYDSSRGGFWV, | (SEQ ID NO: 12) |
| SSYVRSGTRV, | (SEQ ID NO: 18) |
| LQHNSYPYT, | (SEQ ID NO: 24) |
| QQSYSTPAT, | (SEQ ID NO: 30) |
| QQYGRSPLT, or | (SEQ ID NO: 36) |
| HQYGSSPQT. | (SEQ ID NO: 42) |

In some embodiments, CDRH3 comprises at least one amino acid substitution when compared to SEQ ID NO: 3, 9, 15, 21, 27, 33, or 39. In some embodiments, CDRL3 comprises at least one amino acid substitution when compared to SEQ ID NO: 6, 12, 18, 24, 30, 36, or 42.

In some embodiments, CDRH1 comprises an amino acid sequence at least 60% identical to:

| | |
|---|---|
| GFTVSSNY, | (SEQ ID NO: 1) |
| GYIFEAYG, | (SEQ ID NO: 7) |
| GFAFSTYV, | (SEQ ID NO: 13) |
| GGSISSGSYY, | (SEQ ID NO: 19) |
| GFTFSTYV, | (SEQ ID NO: 25) | and/or
CDRL1 comprises an amino acid sequence at least 60% identical to:

SSDVG, (SEQ ID NO: 4)

TSNIGAGYE, (SEQ ID NO: 10)

SSDVGAYNY, (SEQ ID NO: 16)

QGIRND, (SEQ ID NO: 22)

QSISSY, (SEQ ID NO: 28)

QSVYANH, (SEQ ID NO: 34)
or

QSVTNIY. (SEQ ID NO: 40)

In some embodiments, CDRH1 comprises at least one amino acid substitution when compared to SEQ ID NO: 1, 7, 13, 19, 25, 31, or 37. In some embodiments, the CDRL1 comprises at least one amino acid substitution when compared to SEQ ID NO: 4, 10, 16, 22, 28, 34, or 40.

In some embodiments, CDRH2 comprises an amino acid sequence at least 60% identical to:

IYTGGGT, (SEQ ID NO: 2)

ISVFNGDR, (SEQ ID NO: 8)

ISHEGSDK, (SEQ ID NO: 14)

IYMSGTT, (SEQ ID NO: 20)

IWYDGSNK, (SEQ ID NO: 26)

ISGDGSST, (SEQ ID NO: 32)
or

VVPVFDTR; (SEQ ID NO: 38)

CDRL2 comprises an amino acid sequence at least 60% identical to:

EVT, (SEQ ID NO: 5)

GNT, (SEQ ID NO: 11)

EVK, (SEQ ID NO: 17)

AAS, (SEQ ID NO: 23)

AAS, (SEQ ID NO: 29)

GAS, (SEQ ID NO: 35)
or

GAS. (SEQ ID NO: 41)

In some embodiments, CDRH2 comprises at least one amino acid substitution when compared to SEQ ID NO: 2, 8, 14, 20, 26, 32, or 38. In some embodiments, the CDRL2 comprises at least one amino acid substitution when compared to SEQ ID NO: 5, 11, 17, 23, 29, 35, or 41.

In some embodiments, VH comprises an amino acid sequence selected from the group consisting of SEQ ID NO: 43, 45, 47, 49, 51, 53, and 55. In some embodiments, the VL comprises an amino acid sequence selected from the group consisting of SEQ ID NO: 44, 46, 48, 50, 52, 54, and 56.

In some embodiments, the antibody comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH1 is GFTVSSNY, (SEQ ID NO: 1)

CDRH2 is IYTGGGT, (SEQ ID NO: 2)

CDRH3 is AREAPFTAALLYY, (SEQ ID NO: 3)

CDRL1 is SSDVG, (SEQ ID NO: 4)

CDRL2 is EVT, (SEQ ID NO: 5)
and

CDRL3 is SSYAGNNNRVV. (SEQ ID NO: 6)

In some embodiments, the antibody comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH1 is GYIFEAYG, (SEQ ID NO: 7)

CDRH2 is ISVFNGDR, (SEQ ID NO: 8)

CDRH3 is ATGAELLSAFGV, (SEQ ID NO: 9)

CDRL1 is TSNIGAGYE, (SEQ ID NO: 10)

CDRL2 is GNT, (SEQ ID NO: 11)
and

CDRL3 is QSYDSSRGGFWV. (SEQ ID NO: 12)

In some embodiments, the antibody comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH1 is GFAFSTYV, (SEQ ID NO: 13)

CDRH2 is ISHEGSDK, (SEQ ID NO: 14)

CDRH3 is AKEGPRDYYYYGWDV, (SEQ ID NO: 15)

CDRL1 is SSDVGAYNY, (SEQ ID NO: 16)

CDRL2 is EVK, (SEQ ID NO: 17)
and

CDRL3 is SSYVRSGTRV. (SEQ ID NO: 18)

In some embodiments, the antibody comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH1 is GGSISSGSYY, (SEQ ID NO: 19)

CDRH2 is IYMSGTT, (SEQ ID NO: 20)

CDRH3 is ARDPYNWNANYYIDV, (SEQ ID NO: 21)

CDRL1 is QGIRND, (SEQ ID NO: 22)

CDRL2 is AAS, (SEQ ID NO: 23)
and

CDRL3 is LQHNSYPYT. (SEQ ID NO: 24)

In some embodiments, the antibody comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH1 is GFTFSTYV, (SEQ ID NO: 25)

CDRH2 is IWYDGSNK, (SEQ ID NO: 26)

CDRH3 is ARDAGSDAFDI, (SEQ ID NO: 27)

CDRL1 is QSISSY, (SEQ ID NO: 28)

CDRL2 is AAS, (SEQ ID NO: 29)
and

CDRL3 is QQSYSTPAT. (SEQ ID NO: 30)

In some embodiments, the antibody comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH1 is GFPFSNYW, (SEQ ID NO: 31)

CDRH2 is ISGDGSST, (SEQ ID NO: 32)

CDRH3 is ARVQLLADDVLDI, (SEQ ID NO: 33)

CDRL1 is QSVYANH, (SEQ ID NO: 34)

CDRL2 is GAS, (SEQ ID NO: 35)
and

CDRL3 is QQYGRSPLT. (SEQ ID NO: 36)

In some embodiments, the antibody comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH1 is GGIVHSYS, (SEQ ID NO: 37)

CDRH2 is VVPVFDTR, (SEQ ID NO: 38)

CDRH3 is GRLTYHYDSSGFVSTVGNALDV, (SEQ ID NO: 39)

CDRL1 is QSVTNIY, (SEQ ID NO: 40)

CDRL2 is GAS, (SEQ ID NO: 41)
and

CDRL3 is HQYGSSPQT. (SEQ ID NO: 42)

In some embodiments, the antibody comprises a light chain variable region (VL) and/or a heavy chain variable region (VH), wherein:

VH is SEQ ID NO: 43,
and

VL is SEQ ID NO: 44.

In some embodiments, the antibody comprises a light chain variable region (VL) and/or a heavy chain variable region (VH), wherein:

```
VH is SEQ ID NO: 45,
and

VL is SEQ ID NO: 46.
```

In some embodiments, the antibody comprises a light chain variable region (VL) and/or a heavy chain variable region (VH), wherein:

```
VH is SEQ ID NO: 47,
and

VL is SEQ ID NO: 48.
```

In some embodiments, the antibody comprises a light chain variable region (VL) and/or a heavy chain variable region (VH), wherein:

```
VH is SEQ ID NO: 49,
and

VL is SEQ ID NO: 50.
```

In some embodiments, the antibody comprises a light chain variable region (VL) and/or a heavy chain variable region (VH), wherein:

```
VH is SEQ ID NO: 51,
and

VL is SEQ ID NO: 52.
```

In some embodiments, the antibody comprises a light chain variable region (VL) and/or a heavy chain variable region (VH), wherein:

```
VH is SEQ ID NO: 53,
and

VL is SEQ ID NO: 54.
```

In some embodiments, the antibody comprises a light chain variable region (VL) and/or a heavy chain variable region (VH), wherein:

```
VH is SEQ ID NO: 55,
and

VL is SEQ ID NO: 56.
```

In some aspects, disclosed herein is a nucleic acid encoding a recombinant antibody as disclosed herein.

In some aspects, disclosed herein is a recombinant expression cassette or plasmid comprising a sequence to express a VL and/or VH disclosed herein.

In some aspects, disclosed herein is a host cell comprising an expression cassette or a plasmid as described herein.

In some aspects, disclosed herein is a method of producing an antibody, comprising cultivating or maintaining a host cell of under conditions to produce the antibody.

In some aspects, disclosed herein is a method of treating lung cancer, comprising administering to a subject in need thereof a therapeutically effective amount of a recombinant antibody as disclosed herein.

In some embodiments, the lung cancer is non-small cell lung cancer (NSCLC). In some embodiments, the lung cancer is small cell lung cancer (SCLC).

BRIEF DESCRIPTION OF THE DRAWINGS

The accompanying figures, which are incorporated in and constitute a part of this specification, illustrate several aspects described below.

(FIG. 5A) Antibodies are incubated with cells, washed, then detected with secondary anti-human FITC antibody in. Plots show data transformed into MFI as a function of antibody concentration for adenocarcinoma cell lines (FIG. 5B) and bronchial epithelial cell lines (FIG. 5C).

FIG. 6A shows a CD19+, antigen+B cell population from a human tumor sample. FIG. 6B shows a representative lambda light chain amplified by PCR. FIG. 6C shows that D5 mAb expressed recombinantly binds in a dose-dependent manner to VEGF protein. FIG. 6D shows D5 antibody competes with the same epitope as FDA-approved anti-VEGF antibody, bevacizumab (AVASTIN®).

DETAILED DESCRIPTION

Figure 1:
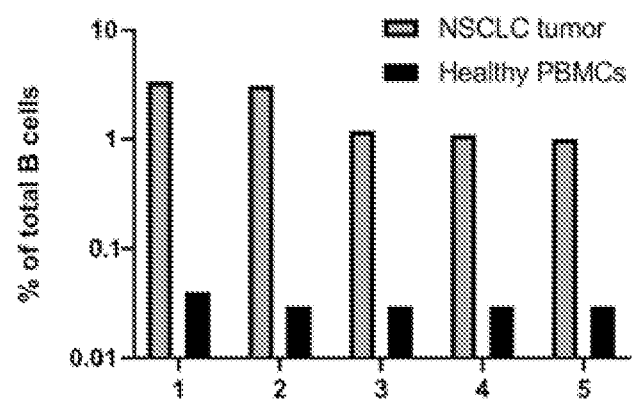
FIG. 1 shows the most abundant B-cell lineages from NSCLC tumor (grey bars) vs. healthy PBMC (black bars) samples. The five most abundant lineages (x-axis) are shown with the respective % total B cells (y-axis; log-scale) for each sample.

Disclosed herein are therapeutic antibodies and methods for treating lung cancer. As described herein, B cells were isolated from human lung cancer tissue and recovered B-cell receptor (BCR) sequences were identified by paired heavy and light chain single cell RNA sequencing. From these experiments, clonally expanded B-cell populations and convergent BCR sequences shared between different patients were identified. The inventors have also demonstrated that the recombinant antibodies described herein bind cultured lung cancer cell lines in a dose-dependent manner. These novel antibodies provide for new and improved therapeutic and diagnostic antibodies.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise.

The following definitions are provided for the full understanding of terms used in this specification.

Terminology

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used herein, the term "subject" or "host" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a human.

"Nucleotide," "nucleoside," "nucleotide residue," and "nucleoside residue," as used herein, can mean a deoxyribonucleotide, ribonucleotide residue, or another similar nucleoside analogue. A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3-AMP (3'-adenosine monophosphate) or 5'-GMP (5'-guanosine monophosphate). There are many varieties of these types of molecules available in the art and available herein.

The method and the system disclosed here including the use of primers, which are capable of interacting with the disclosed nucleic acids, such as the antigen barcode as disclosed herein. In certain embodiments the primers are used to support DNA amplification reactions. Typically, the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically, the disclosed primers hybridize with the disclosed nucleic acids or region of the nucleic acids or they hybridize with the complement of the nucleic acids or complement of a region of the nucleic acids.

The term "amplification" refers to the production of one or more copies of a genetic fragment or target sequence, specifically the "amplicon". As it refers to the product of an amplification reaction, amplicon is used interchangeably with common laboratory terms, such as "PCR product."

The term "polypeptide" refers to a compound made up of a single chain of D- or L-amino acids or a mixture of D- and L-amino acids joined by peptide bonds.

As used herein, the term "antigen" refers to a molecule that is capable of binding to an antibody. In some embodiments, the antigen stimulates an immune response such as by production of antibodies specific for the antigen.

In the present invention, "specific for" and "specificity" means a condition where one of the molecules is involved in selective binding. Accordingly, an antibody that is specific for one antigen selectively binds that antigen and not other antigens.

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof. The antibodies can be tested for their desired activity using the in vitro assays described herein, or by analogous methods, after which their in vivo therapeutic and/or prophylactic activities are tested according to known clinical testing methods. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

Each antibody molecule is made up of the protein products of two genes: heavy-chain gene and light-chain gene. The heavy-chain gene is constructed through somatic recombination of V, D, and J gene segments. In human, there are 51 VH, 27 DH, 6 JH, 9 CH gene segments on human chromosome 14. The light-chain gene is constructed through somatic recombination of V and J gene segments. There are 40 Vκ, 31 Vκ, 5 Jκ, 4 Jλ gene segments on human chromosome 14 (80 VJ). The heavy-chain constant domains that correspond to the different classes of immunoglobulins are called α, δ, ε, γ, and μ, respectively. The "light chains" of antibodies from any vertebrate species can be assigned to one of two clearly distinct types, called kappa (κ) and lambda (λ), based on the amino acid sequences of their constant domains.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

The disclosed monoclonal antibodies can be made using any procedure which produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

As used herein, the term "antibody or antigen binding fragment thereof" or "antibody or fragments thereof" encompasses chimeric antibodies and hybrid antibodies, with dual or multiple antigen or epitope specificities, and fragments, such as F(ab')2, Fab', Fab, Fv, sFv, scFv and the like, including hybrid fragments. Thus, fragments of the antibodies that retain the ability to bind their specific antigens are provided. Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or antigen binding fragment thereof" are conjugates of antibody fragments and antigen binding proteins (single chain antibodies). Also included within the meaning of "antibody or antigen binding fragment thereof" are immunoglobulin single variable domains, such as for example a nanobody.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

The terms "antigen binding site", "binding site" and "binding domain" refer to the specific elements, parts or amino acid residues of a polypeptide, such as an antibody, that bind the antigenic determinant or epitope.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations, κ and λ light chains refer to the two major antibody light chain isotypes.

The term "CDR" as used herein refers to the "complementarity determining regions" of the antibody which consist of the antigen binding loops. (Kabat E. A. et al., (1991) Sequences of proteins of immunological interest. NIH Publication 91-3242). Each of the two variable domains of an antibody Fv fragment contain, for example, three CDRs.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen-binding regions. The amino acid sequence boundaries of a CDR can be determined by one of skill in the art using any of a number of known numbering schemes, including those described by Kabat et al., supra ("Kabat" numbering scheme); Al-Lazikani et al., 1997. J. Mol. Biol., 273:927-948 ("Chothia" numbering scheme); MacCallum et al., 1996, J. Mol. Biol, 262:732-745 ("Contact" numbering scheme); Lefranc et al., Dev. Comp. Immunol., 2003, 27:55-77 ("IMGT" numbering scheme); and Honegge and Plückthun, J. Mol. Biol., 2001, 309:657-70 ("AHo" numbering scheme); each of which is incorporated by reference in its entirety.

"Composition" refers to any agent that has a beneficial biological effect. Beneficial biological effects include both therapeutic effects, e.g., treatment of a disorder or other undesirable physiological condition, and prophylactic effects, e.g., prevention of a disorder or other undesirable physiological condition. The terms also encompass pharmaceutically acceptable, pharmacologically active derivatives of beneficial agents specifically mentioned herein, including, but not limited to, a bacterium, a vector, polynucleotide, cells, salts, esters, amides, proagents, active metabolites, isomers, fragments, analogs, and the like. When the term "composition" is used, then, or when a particular composition is specifically identified, it is to be understood that the term includes the composition per se as well as pharmaceutically acceptable, pharmacologically active vector, polynucleotide, salts, esters, amides, proagents, conjugates, active metabolites, isomers, fragments, analogs, etc.

"Effective amount" encompasses, without limitation, an amount that can ameliorate, reverse, mitigate, prevent, or diagnose a symptom or sign of a medical condition or disorder. Unless dictated otherwise, explicitly or by context, an "effective amount" is not limited to a minimal amount sufficient to ameliorate a condition. The severity of a disease or disorder, as well as the ability of a treatment to prevent, treat, or mitigate, the disease or disorder can be measured, without implying any limitation, by a biomarker or by a clinical parameter.

The "fragments" or "functional fragments," whether attached to other sequences or not, can include insertions, deletions, substitutions, or other selected modifications of particular regions or specific amino acids residues, provided the activity of the fragment is not significantly altered or impaired compared to the nonmodified peptide or protein. These modifications can provide for some additional property, such as to remove or add amino acids capable of disulfide bonding, to increase its bio-longevity, to alter its secretory characteristics, etc.

The term "identity" or "homology" shall be construed to mean the percentage of nucleotide bases or amino acid residues in the candidate sequence that are identical with the bases or residues of a corresponding sequence to which it is compared, after aligning the sequences and introducing gaps, if necessary to achieve the maximum percent identity for the entire sequence, and not considering any conservative substitutions as part of the sequence identity. A polynucleotide or polynucleotide region (or a polypeptide or polypeptide region) that has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art. Such alignment can be provided using, for instance, the method of Needleman et al. (1970) J. Mol. Biol. 48: 443-453, implemented conveniently by computer programs such as the Align program (DNAstar, Inc.).

The term "increased" or "increase" as used herein generally means an increase by a staticaly significant amount; for example, "increased" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the terms "nanobody", "$V_HH$", "$V_HH$ antibody fragment" and "single domain antibody" are used indifferently and designate a variable domain of a single heavy chain of an antibody of the type found in Camelidae, which are without any light chains, such as those derived from Camelids as described in PCT Publication No. WO 94/04678, which is incorporated by reference in its entirety.

The term "reduced", "reduce", "reduction", or "decrease" as used herein generally means a decrease by a statistically significant amount. However, for avoidance of doubt, "reduced" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

"Nucleotide," "nucleoside," "nucleotide residue," and "nucleoside residue," as used herein, can mean a deoxyribonucleotide, ribonucleotide residue, or another similar nucleoside analogue. A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3-AMP (3'-adenosine monophosphate) or 5'-GMP (5'-guanosine monophosphate). There are many varieties of these types of molecules available in the art and available herein.

The method and the system disclosed here including the use of primers, which are capable of interacting with the disclosed nucleic acids, such as the antigen barcode as disclosed herein. In certain embodiments the primers are used to support DNA amplification reactions. Typically, the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically, the disclosed primers hybridize with the disclosed nucleic acids or region of the nucleic acids or they hybridize with the complement of the nucleic acids or complement of a region of the nucleic acids.

The term "amplification" refers to the production of one or more copies of a genetic fragment or target sequence, specifically the "amplicon". As it refers to the product of an amplification reaction, amplicon is used interchangeably with common laboratory terms, such as "PCR product."

The term "polypeptide" refers to a compound made up of a single chain of D- or L-amino acids or a mixture of D- and L-amino acids joined by peptide bonds.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA.

An "expression cassette" refers to a DNA coding sequence or segment of DNA that code for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct".

Expression vectors comprise the expression cassette and additionally usually comprise an origin for autonomous replication in the host cells or a genome integration site, one or more selectable markers (e.g. an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together. The term "vector" as used herein includes autonomously replicating nucleotide sequences as well as genome integrating nucleotide sequences. A common type of vector is a "plasmid", which generally is a self-contained molecule of double-stranded DNA that can readily accept additional (foreign) DNA and which can readily be introduced into a suitable host cell. A plasmid vector often contains coding DNA and promoter DNA and has one or more restriction sites suitable for inserting foreign DNA. Specifically, the term "vector" or "plasmid" refers to a vehicle by which a DNA or RNA sequence (e.g. a foreign gene) can be introduced into a host cell, so as to transform the host and promote expression (e.g. transcription and translation) of the introduced sequence.

The term "host cell" as used herein shall refer to primary subject cells trans-formed to produce a particular recombinant protein, such as an antibody as described herein, and any progeny thereof. It should be understood that not all progeny are exactly identical to the parental cell (due to deliberate or inadvertent mutations or differences in environment), however, such altered progeny are included in these terms, so long as the progeny retain the same functionality as that of the originally transformed cell. The term "host cell line" refers to a cell line of host cells as used for expressing a recombinant gene to produce recombinant polypeptides such as recombinant antibodies. The term "cell line" as used herein refers to an established clone of a particular cell type that has acquired the ability to proliferate over a prolonged period of time. Such host cell or host cell line may be maintained in cell culture and/or cultivated to produce a recombinant polypeptide.

The term "gene" or "gene sequence" refers to the coding sequence or control sequence, or fragments thereof. A gene may include any combination of coding sequence and control sequence, or fragments thereof. Thus, a "gene" as referred to herein may be all or part of a native gene. A polynucleotide sequence as referred to herein may be used interchangeably with the term "gene", or may include any coding sequence, non-coding sequence or control sequence, fragments thereof, and combinations thereof. The term "gene" or "gene sequence" includes, for example, control sequences upstream of the coding sequence (for example, the ribosome binding site).

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents.

As used herein, the term "carrier" encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., *Remington's Pharmaceutical Sciences,* 21st Edition, ed. University of the Sciences in Philadelphia, Lippincott, Williams & Wilkins, Philadelphia, PA, 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, New Jersey), polyethylene glycol (PEG), and PLURONICS™ (BASF; Florham Park, NJ). To provide for the administration of such dosages for the desired therapeutic treatment, compositions disclosed herein can advantageously comprise between about 0.1% and 99% by weight of the total of one or more of the subject compounds based on the weight of the total composition including carrier or diluent.

The term "specificity" refers to the number of different types of antigens or antigenic determinants to which a particular antigen-binding molecule (such as the recombinant antibody of the invention) can bind. As used herein, the term "specifically binds," as used herein with respect to a recombinant antibody refers to the recombinant antibody's preferential binding to one or more epitopes as compared with other epitopes. Specific binding can depend upon binding affinity and the stringency of the conditions under which the binding is conducted. In one example, an antibody specifically binds an epitope when there is high affinity binding under stringent conditions.

"Therapeutically effective amount" refers to the amount of a composition such as recombinant antibody that will elicit the biological or medical response of a tissue, system, animal, or human that is being sought by the researcher, veterinarian, medical doctor or other clinician over a generalized period of time. In some instances, a desired biological or medical response is achieved following administration of multiple dosages of the composition to the subject over a period of days, weeks, or years. The therapeutically effective amount will vary depending on the composition, the disorder or conditions and its severity, the route of administration, time of administration, rate of excretion, drug combination, judgment of the treating physician, dosage form, and the age, weight, general health, sex and/or diet of the subject to be treated. The therapeutically effective amount of recombinant antibodies as described herein can be determined by one of ordinary skill in the art.

A therapeutically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. Measured or measurable parameters include clinically detectable markers of disease, for example, elevated or depressed levels of a biological marker, such as decreased viral titers, decreased viral RNA levels, increase in CD4 T lymphocyte counts, and/or prolonged survival of a subject. It will be understood, that the total daily usage of the compositions and formulations as disclosed herein will be decided by the attending physician within the scope of sound medical judgment. The exact amount required will vary depending on factors such as the type of disease being treated.

The terms "treat," "treating," "treatment," and grammatical variations thereof as used herein, include partially or completely delaying, alleviating, mitigating or reducing the intensity of one or more attendant symptoms of a cancer or condition and/or alleviating, mitigating or impeding one or more causes of a cancer. Treatments according to the invention may be applied preventively, prophylactically, palliatively or remedially. Prophylactic treatments are administered to a subject prior to onset (e.g., before obvious signs of an infection), during early onset (e.g., upon initial signs and symptoms of an infection), after an established development of an infection, or during chronic infection. Prophylactic administration can occur for several minutes to months prior to the manifestation of an infection.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

Antibodies and Compositions

In some aspects, disclosed herein is a recombinant antibody, wherein the antibody or antigen binding fragment thereof comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH3 comprises an amino acid sequence at least 60% identical to:

```
                         (SEQ ID NO: 3)
AREAPFTAALLYY, (SEQ ID NO: 9)
ATGAELLSAFGV, (SEQ ID NO: 15)
AKEGPRDYYYYGWDV, (SEQ ID NO: 21)
ARDPYNWNANYYIDV, (SEQ ID NO: 27)
ARDAGSDAFDI, (SEQ ID NO: 33)
ARVQLLADDVLDI,
or
                         (SEQ ID NO: 39)
GRLTYHYDSSGFVSTVGNALDV;
```

CDRL3 comprises an amino acid sequence at least 60% identical to:

```
                         (SEQ ID NO: 6)
SSYAGNNNRVV, (SEQ ID NO: 12)
QSYDSSRGGFWV, (SEQ ID NO: 18)
SSYVRSGTRV, (SEQ ID NO: 24)
LQHNSYPYT, (SEQ ID NO: 30)
QQSYSTPAT, (SEQ ID NO: 36)
QQYGRSPLT,
or
                         (SEQ ID NO: 42)
HQYGSSPQT.
```

In some embodiments, CDRH3 comprises at least one amino acid substitution when compared to SEQ ID NO: 3, 9, 15, 21, 27, 33, or 39. In some embodiments, CDRL3 comprises at least one amino acid substitution when compared to SEQ ID NO: 6, 12, 18, 24, 30, 36, or 42.

In some embodiments, CDRH1 comprises an amino acid sequence at least 60% identical to:

```
                         (SEQ ID NO: 1)
GFTVSSNY, (SEQ ID NO: 7)
GYIFEAYG, (SEQ ID NO: 13)
GFAFSTYV, (SEQ ID NO: 19)
GGSISSGSYY, (SEQ ID NO: 25)
GFTFSTYV, (SEQ ID NO: 31)
GFPFSNYW,
or
                         (SEQ ID NO: 37)
GGIVHSYS;
``` and/or
CDRL1 comprises an amino acid sequence at least 60% identical to:

SSDVG, (SEQ ID NO: 4)

TSNIGAGYE, (SEQ ID NO: 10)

SSDVGAYNY, (SEQ ID NO: 16)

QGIRND, (SEQ ID NO: 22)

QSISSY, (SEQ ID NO: 28)

QSVYANH, (SEQ ID NO: 34)
or

QSVTNIY. (SEQ ID NO: 40)

In some embodiments, CDRH1 comprises at least one amino acid substitution when compared to SEQ ID NO: 1, 7, 13, 19, 25, 31, or 37. In some embodiments, the CDRL1 comprises at least one amino acid substitution when compared to SEQ ID NO: 4, 10, 16, 22, 28, 34, or 40.

In some embodiments, CDRH2 comprises an amino acid sequence at least 60% identical to:

IYTGGGT, (SEQ ID NO: 2)

ISVFNGDR, (SEQ ID NO: 8)

ISHEGSDK, (SEQ ID NO: 14)

IYMSGTT, (SEQ ID NO: 20)

IWYDGSNK, (SEQ ID NO: 26)

ISGDGSST, (SEQ ID NO: 32)
or

VVPVFDTR; (SEQ ID NO: 38)

and/or
CDRL2 comprises an amino acid sequence at least 60% identical to:

EVT, (SEQ ID NO: 5)

GNT, (SEQ ID NO: 11)

EVK, (SEQ ID NO: 17)

AAS, (SEQ ID NO: 23)

AAS, (SEQ ID NO: 29)

GAS, (SEQ ID NO: 35)
or

GAS. (SEQ ID NO: 41)

In some embodiments, CDRH2 comprises at least one amino acid substitution when compared to SEQ ID NO: 2, 8, 14, 20, 26, 32, or 38. In some embodiments, the CDRL2 comprises at least one amino acid substitution when compared to SEQ ID NO: 5, 11, 17, 23, 29, 35, or 41.

In some embodiments, VH comprises an amino acid sequence selected from the group consisting of SEQ ID NO: 43, 45, 47, 49, 51, 53, and 55. In some embodiments, the VL comprises an amino acid sequence selected from the group consisting of SEQ ID NO: 44, 46, 48, 50, 52, 54, and 56.

In some embodiments, the antibody or antigen binding fragment thereof comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH1 is GFTVSSNY, (SEQ ID NO: 1)

CDRH2 is IYTGGGT, (SEQ ID NO: 2)

CDRH3 is AREAPFTAALLYY, (SEQ ID NO: 3)

CDRL1 is SSDVG, (SEQ ID NO: 4)

CDRL2 is EVT, (SEQ ID NO: 5)
and

CDRL3 is SSYAGNNNRVV. (SEQ ID NO: 6)

In some embodiments, the antibody or antigen binding fragment thereof comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH1 is GYIFEAYG, (SEQ ID NO: 7)

CDRH2 is ISVFNGDR, (SEQ ID NO: 8)

CDRH3 is ATGAELLSAFGV, (SEQ ID NO: 9)

CDRL1 is TSNIGAGYE, (SEQ ID NO: 10)

CDRL2 is GNT, (SEQ ID NO: 11)
and

CDRL3 is QSYDSSRGGFWV. (SEQ ID NO: 12)

In some embodiments, the antibody or antigen binding fragment thereof comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

```
                            (SEQ ID NO: 13)
CDRH1 is GFAFSTYV, (SEQ ID NO: 14)
CDRH2 is ISHEGSDK, (SEQ ID NO: 15)
CDRH3 is AKEGPRDYYYYGWDV, (SEQ ID NO: 16)
CDRL1 is SSDVGAYNY, (SEQ ID NO: 17)
CDRL2 is EVK,
and (SEQ ID NO: 18)
CDRL3 is SSYVRSGTRV.
```

In some embodiments, the antibody or antigen binding fragment thereof comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

```
                            (SEQ ID NO: 19)
CDRH1 is GGSISSGSYY, (SEQ ID NO: 20)
CDRH2 is IYMSGTT, (SEQ ID NO: 21)
CDRH3 is ARDPYNWNANYYIDV, (SEQ ID NO: 22)
CDRL1 is QGIRND, (SEQ ID NO: 23)
CDRL2 is AAS,
and (SEQ ID NO: 24)
CDRL3 is LQHNSYPYT.
```

In some embodiments, the antibody or antigen binding fragment thereof comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

```
                            (SEQ ID NO: 25)
CDRH1 is GFTFSTYV, (SEQ ID NO: 26)
CDRH2 is IWYDGSNK, (SEQ ID NO: 27)
CDRH3 is ARDAGSDAFDI, (SEQ ID NO: 28)
CDRL1 is QSISSY, (SEQ ID NO: 29)
```

```
CDRL2 is AAS,
and (SEQ ID NO: 30)
CDRL3 is QQSYSTPAT.
```

In some embodiments, the antibody or antigen binding fragment thereof comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

```
                            (SEQ ID NO: 31)
CDRH1 is GFPFSNYW, (SEQ ID NO: 32)
CDRH2 is ISGDGSST, (SEQ ID NO: 33)
CDRH3 is ARVQLLADDVLDI, (SEQ ID NO: 34)
CDRL1 is QSVYANH, (SEQ ID NO: 35)
CDRL2 is GAS,
and (SEQ ID NO: 36)
CDRL3 is QQYGRSPLT.
```

In some embodiments, the antibody or antigen binding fragment thereof comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

```
                            (SEQ ID NO: 37)
CDRH1 is GGIVHSYS, (SEQ ID NO: 38)
CDRH2 is VVPVFDTR, (SEQ ID NO: 39)
CDRH3 is GRLTYHYDSSGFVSTVGNALDV, (SEQ ID NO: 40)
CDRL1 is QSVTNIY, (SEQ ID NO: 41)
CDRL2 is GAS,
and (SEQ ID NO: 42)
CDRL3 is HQYGSSPQT.
```

In some embodiments, the antibody or antigen binding fragment thereof comprises a light chain variable region (VL) and/or a heavy chain variable region (VH), wherein:

```
VH is SEQ ID NO: 43,
and

VL is SEQ ID NO: 44.
```

In some embodiments, the antibody or antigen binding fragment thereof comprises a light chain variable region (VL) and/or a heavy chain variable region (VH), wherein:

VH is SEQ ID NO: 45,
and

VL is SEQ ID NO: 46.

In some embodiments, the antibody or antigen binding fragment thereof comprises a light chain variable region (VL) and/or a heavy chain variable region (VH), wherein:

VH is SEQ ID NO: 47,
and

VL is SEQ ID NO: 48.

In some embodiments, the antibody or antigen binding fragment thereof comprises a light chain variable region (VL) and/or a heavy chain variable region (VH), wherein:

VH is SEQ ID NO: 49,
and

VL is SEQ ID NO: 50.

In some embodiments, the antibody or antigen binding fragment thereof comprises a light chain variable region (VL) and/or a heavy chain variable region (VH), wherein:

VH is SEQ ID NO: 51,
and

VL is SEQ ID NO: 52.

In some embodiments, the antibody or antigen binding fragment thereof comprises a light chain variable region (VL) and/or a heavy chain variable region (VH), wherein:

VH is SEQ ID NO: 53,
and

VL is SEQ ID NO: 54.

In some embodiments, the antibody or antigen binding fragment thereof comprises a light chain variable region (VL) and/or a heavy chain variable region (VH), wherein:

VH is SEQ ID NO: 55,
and

VL is SEQ ID NO: 56.

In some embodiments, CDRH1 comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to GFTVSSNY (SEQ ID NO:1), GYIFEAYG (SEQ ID NO:7), GFAFSTYV (SEQ ID NO:13), GGSISSGSYY (SEQ ID NO:19), GFTFSTYV (SEQ ID NO:25), GFPFSNYW (SEQ ID NO:31), or GGIVHSYS (SEQ ID NO:37). In some embodiments, CDRH1 comprises SEQ ID NO:1. In some embodiments, CDRH1 comprises SEQ ID NO:7. In some embodiments, CDRH1 comprises SEQ ID NO:13. In some embodiments, CDRH1 comprises SEQ ID NO:19. In some embodiments, CDRH1 comprises SEQ ID NO:25. In some embodiments, CDRH1 comprises SEQ ID NO:31. In some embodiments, CDRH1 comprises SEQ ID NO:37.

In some embodiments, CDRH2 comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to IYTGGGT (SEQ ID NO:2), ISVFNGDR (SEQ ID NO:8), ISHEGSDK (SEQ ID NO:14), IYMSGTT (SEQ ID NO:20), IWYDGSNK (SEQ ID NO:26), ISGDGSST (SEQ ID NO:32), or VVPVFDTR (SEQ ID NO:38). In some embodiments, CDRH2 comprises SEQ ID NO:2. In some embodiments, CDRH2 comprises SEQ ID NO:8. In some embodiments, CDRH2 comprises SEQ ID NO:14. In some embodiments, CDRH2 comprises SEQ ID NO:20. In some embodiments, CDRH2 comprises SEQ ID NO:26. In some embodiments, CDRH2 comprises SEQ ID NO:32. In some embodiments, CDRH2 comprises SEQ ID NO:38.

In some embodiments, CDRH3 comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to AREAPFTAALYY (SEQ ID NO:3), ATGAELLSAFGV (SEQ ID NO:9), AKEG-PRDYYYYGWDV (SEQ ID NO:15), ARDPYNWNANYYIDV (SEQ ID NO:21), ARDAGS-DAFDI (SEQ ID NO:27), ARVQLLADDVLDI (SEQ ID NO:33), or GRLTYHYDSSGFVSTVGNALDV (SEQ ID NO:39). In some embodiments, CDRH3 comprises SEQ ID NO:3. In some embodiments, CDRH3 comprises SEQ ID NO:9. In some embodiments, CDRH3 comprises SEQ ID NO:15. In some embodiments, CDRH3 comprises SEQ ID NO:21. In some embodiments, CDRH3 comprises SEQ ID NO:27. In some embodiments, CDRH3 comprises SEQ ID NO:33. In some embodiments, CDRH3 comprises SEQ ID NO:39.

In some embodiments, CDRL1 comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SSDVG (SEQ ID NO:4), TSNIGAGYE (SEQ ID NO:10), SSDVGAYNY (SEQ ID NO:16), QGIRND (SEQ ID NO:22), QSISSY (SEQ ID NO:28), QSVYANH (SEQ ID NO:34), or QSVTNIY (SEQ ID NO:40). In some embodiments, CDRL1 comprises SEQ ID NO:4. In some embodiments, CDRL1 comprises SEQ ID NO:10. In some embodiments, CDRL1 comprises SEQ ID NO:16. In some embodiments, CDRL1 comprises SEQ ID NO:22. In some embodiments, CDRL1 comprises SEQ ID NO:28. In some embodiments, CDRL1 comprises SEQ ID NO:34. In some embodiments, CDRL1 comprises SEQ ID NO:40.

In some embodiments, CDRL2 comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to EVT (SEQ ID NO:5), GNT (SEQ ID NO:11), EVK (SEQ ID NO:17), AAS (SEQ ID NO:23), AAS (SEQ ID NO:29), GAS (SEQ ID NO:35), or GAS (SEQ ID NO:41). In some embodiments, CDRL2 comprises SEQ ID NO:5. In some embodiments, CDRL2 comprises SEQ ID NO:11. In some embodiments, CDRL2 comprises SEQ ID NO:17. In some embodiments, CDRL2 comprises SEQ ID NO:23. In some embodiments, CDRL2 comprises SEQ ID NO:29. In some embodiments, CDRL2 comprises SEQ ID NO:35. In some embodiments, CDRL2 comprises SEQ ID NO:41.

In some embodiments, CDRL3 comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SSYAGNNNRVV (SEQ ID NO:6), QSYDSSRGGFWV (SEQ ID NO:12), SSYVRSGTRV (SEQ ID NO:18), LQHNSYPYT (SEQ ID NO:24), QQSYSTPAT (SEQ ID NO:30), QQYGRSPLT (SEQ ID NO:36), or HQYGSSPQT (SEQ ID NO:42). In some embodiments, CDRL3 comprises SEQ ID NO:6. In some embodiments, CDRL3 comprises SEQ ID NO:12. In some embodiments, CDRL3 comprises SEQ ID NO:18. In some embodiments, CDRL3 comprises SEQ ID NO:24. In some embodiments, CDRL3 comprises SEQ ID NO:30. In some embodiments, CDRL3 comprises SEQ ID NO:36. In some embodiments, CDRL3 comprises SEQ ID NO:42.

In some embodiments, CDRH3 comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to ARVQLADDVLNI (SEQ ID NO:57), ARPMTTVTPKAFDI (SEQ ID NO:59), ARVQLLADDVLDI (SEQ ID NO:60), ARVQVLADDVLNI (SEQ ID NO:61), ARDPAGDAFDI (SEQ ID NO:62), or ARDPAWGAYDI (SEQ ID NO:63).

In some embodiments, CDRL3 comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to QQYGSSPLT (SEQ ID NO:58).

In some embodiments, VH comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO:43. In some embodiments, VH comprises SEQ ID NO:43.

In some embodiments, VH comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO:45. In some embodiments, VH comprises SEQ ID NO:45.

In some embodiments, VH comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO:47. In some embodiments, VH comprises SEQ ID NO:47.

In some embodiments, VH comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO:49. In some embodiments, VH comprises SEQ ID NO:49.

In some embodiments, VH comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO:51. In some embodiments, VH comprises SEQ ID NO:51.

In some embodiments, VH comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO:53. In some embodiments, VH comprises SEQ ID NO:53.

In some embodiments, VH comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO:55. In some embodiments, VH comprises SEQ ID NO:55.

In some embodiments, VL comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO:44. In some embodiments, VL comprises SEQ ID NO:44.

In some embodiments, VL comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO:46. In some embodiments, VL comprises SEQ ID NO:46.

In some embodiments, VL comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO:48. In some embodiments, VL comprises SEQ ID NO:48.

In some embodiments, VL comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO:50. In some embodiments, VL comprises SEQ ID NO:50.

In some embodiments, VL comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO:52. In some embodiments, VL comprises SEQ ID NO:52.

In some embodiments, VL comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO:54. In some embodiments, VL comprises SEQ ID NO:54.

In some embodiments, VL comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO:56. In some embodiments, VL comprises SEQ ID NO:56.

In some aspects, disclosed herein is a nucleic acid encoding a recombinant antibody or antigen binding fragment thereof as disclosed herein.

In some aspects, disclosed herein is a recombinant expression cassette or plasmid comprising a sequence to express a VL and/or VH disclosed herein.

In some aspects, disclosed herein is a host cell comprising an expression cassette or a plasmid as described herein.

In some embodiments, a CDR sequence (for example CDRL1, CDRL2, CDRL3, CDRH1, CDRH2, or CDRH3) comprises one amino acid mutation, two amino acid mutations, three amino acid mutations, four amino acid mutations, five amino acid mutations, etc. when compared to a CDR sequence as disclosed herein.

In some embodiments, the recombinant antibody is a monoclonal antibody. In some embodiments, the recombinant antibody is an isolated antibody. In some embodiments, the recombinant antibody is an antibody or antigen binding fragment thereof. In some embodiments, combinations of antibodies or antigen binding fragments thereof are used for treating lung cancer.

In some embodiments, the recombinant antibody specifically binds to VEGF. In some embodiments, the recombinant antibody specifically binds to the same epitope on VEGF as bevacizumab (AVASTIN®). In some embodiments, the recombinant antibody competitively inhibits binding of bevacizumab (AVASTIN®) to VEGF.

Methods

In some aspects, disclosed herein is a method of treating lung cancer, comprising administering to a subject in need thereof a therapeutically effective amount of a recombinant antibody or antigen binding fragment thereof, wherein the recombinant antibody or antigen binding fragment thereof comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH3 comprises an amino acid sequence at least 60% identical to:

```
                                    (SEQ ID NO: 3)
AREAPFTAALLYY, (SEQ ID NO: 9)
ATGAELLSAFGV, (SEQ ID NO: 15)
AKEGPRDYYYYGWDV, (SEQ ID NO: 21)
ARDPYNWNANYYIDV, (SEQ ID NO: 27)
ARDAGSDAFDI, (SEQ ID NO: 33)
ARVQLLADDVLDI,
or (SEQ ID NO: 39)
GRLTYHYDSSGFVSTVGNALDV;
```

CDRL3 comprises an amino acid sequence at least 60% identical to:

```
                                    (SEQ ID NO: 6)
SSYAGNNNRVV, (SEQ ID NO: 12)
QSYDSSRGGFWV, (SEQ ID NO: 18)
SSYVRSGTRV, (SEQ ID NO: 24)
LQHNSYPYT, (SEQ ID NO: 30)
QQSYSTPAT, (SEQ ID NO: 36)
QQYGRSPLT,
or (SEQ ID NO: 42)
HQYGSSPQT.
```

In some embodiments, CDRH3 comprises at least one amino acid substitution when compared to SEQ ID NO: 3, 9, 15, 21, 27, 33, or 39. In some embodiments, CDRL3 comprises at least one amino acid substitution when compared to SEQ ID NO: 6, 12, 18, 24, 30, 36, or 42.

In some embodiments, CDRH1 comprises an amino acid sequence at least 60% identical to:

```
                                    (SEQ ID NO: 1)
GFTVSSNY, (SEQ ID NO: 7)
GYIFEAYG, (SEQ ID NO: 13)
GFAFSTYV, (SEQ ID NO: 19)
GGSISSGSYY, (SEQ ID NO: 25)
GFTFSTYV, (SEQ ID NO: 31)
GFPFSNYW,
or (SEQ ID NO: 37)
GGIVHSYS;
``` and/or

CDRL1 comprises an amino acid sequence at least 60% identical to:

```
                                    (SEQ ID NO: 4)
SSDVG, (SEQ ID NO: 10)
TSNIGAGYE, (SEQ ID NO: 16)
SSDVGAYNY, (SEQ ID NO: 22)
QGIRND, (SEQ ID NO: 28)
QSISSY, (SEQ ID NO: 34)
QSVYANH,
or (SEQ ID NO: 40)
QSVTNIY.
```

In some embodiments, CDRH1 comprises at least one amino acid substitution when compared to SEQ ID NO: 1, 7, 13, 19, 25, 31, or 37. In some embodiments, the CDRL1 comprises at least one amino acid substitution when compared to SEQ ID NO: 4, 10, 16, 22, 28, 34, or 40.

In some embodiments, CDRH2 comprises an amino acid sequence at least 60% identical to:

```
                                    (SEQ ID NO: 2)
IYTGGGT, (SEQ ID NO: 8)
ISVFNGDR, (SEQ ID NO: 14)
ISHEGSDK, (SEQ ID NO: 20)
IYMSGTT,
```

-continued

IWYDGSNK, (SEQ ID NO: 26)

ISGDGSST, (SEQ ID NO: 32)
or

VVPVFDTR; (SEQ ID NO: 38)

and/or
CDRL2 comprises an amino acid sequence at least 60% identical to:

EVT, (SEQ ID NO: 5)

GNT, (SEQ ID NO: 11)

EVK, (SEQ ID NO: 17)

AAS, (SEQ ID NO: 23)

AAS, (SEQ ID NO: 29)

GAS, (SEQ ID NO: 35)
or

GAS. (SEQ ID NO: 41)

In some embodiments, CDRH2 comprises at least one amino acid substitution when compared to SEQ ID NO: 2, 8, 14, 20, 26, 32, or 38. In some embodiments, the CDRL2 comprises at least one amino acid substitution when compared to SEQ ID NO: 5, 11, 17, 23, 29, 35, or 41.

In some embodiments, VH comprises an amino acid sequence selected from the group consisting of SEQ ID NO: 43, 45, 47, 49, 51, 53, and 55. In some embodiments, the VL comprises an amino acid sequence selected from the group consisting of SEQ ID NO: 44, 46, 48, 50, 52, 54, and 56.

In some embodiments, the antibody or antigen binding fragment thereof comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH1 is GFTVSSNY, (SEQ ID NO: 1)

CDRH2 is IYTGGGT, (SEQ ID NO: 2)

CDRH3 is AREAPFTAALLYY, (SEQ ID NO: 3)

CDRL1 is SSDVG, (SEQ ID NO: 4)

CDRL2 is EVT, (SEQ ID NO: 5)
and

CDRL3 is SSYAGNNNRVV. (SEQ ID NO: 6)

In some embodiments, the antibody or antigen binding fragment thereof comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH1 is GYIFEAYG, (SEQ ID NO: 7)

CDRH2 is ISVFNGDR, (SEQ ID NO: 8)

CDRH3 is ATGAELLSAFGV, (SEQ ID NO: 9)

CDRL1 is TSNIGAGYE, (SEQ ID NO: 10)

CDRL2 is GNT, (SEQ ID NO: 11)
and

CDRL3 is QSYDSSRGGFWV. (SEQ ID NO: 12)

In some embodiments, the antibody or antigen binding fragment thereof comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH1 is GFAFSTYV, (SEQ ID NO: 13)

CDRH2 is ISHEGSDK, (SEQ ID NO: 14)

CDRH3 is AKEGPRDYYYYGWDV, (SEQ ID NO: 15)

CDRL1 is SSDVGAYNY, (SEQ ID NO: 16)

CDRL2 is EVK, (SEQ ID NO: 17)
and

CDRL3 is SSYVRSGTRV. (SEQ ID NO: 18)

In some embodiments, the antibody or antigen binding fragment thereof comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH1 is GGSISSGSYY, (SEQ ID NO: 19)

CDRH2 is IYMSGTT, (SEQ ID NO: 20)

CDRH3 is ARDPYNWNANYYIDV, (SEQ ID NO: 21)

-continued

CDRL1 is QGIRND, (SEQ ID NO: 22)

CDRL2 is AAS, (SEQ ID NO: 23)
and

CDRL3 is LQHNSYPYT. (SEQ ID NO: 24)

In some embodiments, the antibody or antigen binding fragment thereof comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH1 is GFTFSTYV, (SEQ ID NO: 25)

CDRH2 is IWYDGSNK, (SEQ ID NO: 26)

CDRH3 is ARDAGSDAFDI, (SEQ ID NO: 27)

CDRL1 is QSISSY, (SEQ ID NO: 28)

CDRL2 is AAS, (SEQ ID NO: 29)
and

CDRL3 is QQSYSTPAT. (SEQ ID NO: 30)

In some embodiments, the antibody or antigen binding fragment thereof comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH1 is GFPFSNYW, (SEQ ID NO: 31)

CDRH2 is ISGDGSST, (SEQ ID NO: 32)

CDRH3 is ARVQLLADDVLDI, (SEQ ID NO: 33)

CDRL1 is QSVYANH, (SEQ ID NO: 34)

CDRL2 is GAS, (SEQ ID NO: 35)
and

CDRL3 is QQYGRSPLT. (SEQ ID NO: 36)

In some embodiments, the antibody or antigen binding fragment thereof comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH1 is GGIVHSYS, (SEQ ID NO: 37)

CDRH2 is VVPVFDTR, (SEQ ID NO: 38)

CDRH3 is GRLTYHYDSSGFVSTVGNALDV, (SEQ ID NO: 39)

CDRL1 is QSVTNIY, (SEQ ID NO: 40)

CDRL2 is GAS, (SEQ ID NO: 41)
and

CDRL3 is HQYGSSPQT. (SEQ ID NO: 42)

In some embodiments, the antibody or antigen binding fragment thereof comprises a light chain variable region (VL) and/or a heavy chain variable region (VH), wherein:

VH is SEQ ID NO: 43,
and

VL is SEQ ID NO: 44.

In some embodiments, the antibody or antigen binding fragment thereof comprises a light chain variable region (VL) and/or a heavy chain variable region (VH), wherein:

VH is SEQ ID NO: 45,
and

VL is SEQ ID NO: 46.

In some embodiments, the antibody or antigen binding fragment thereof comprises a light chain variable region (VL) and/or a heavy chain variable region (VH), wherein:

VH is SEQ ID NO: 47,
and

VL is SEQ ID NO: 48.

In some embodiments, the antibody or antigen binding fragment thereof comprises a light chain variable region (VL) and/or a heavy chain variable region (VH), wherein:

VH is SEQ ID NO: 49,
and

VL is SEQ ID NO: 50.

In some embodiments, the antibody or antigen binding fragment thereof comprises a light chain variable region (VL) and/or a heavy chain variable region (VH), wherein:

VH is SEQ ID NO: 51,
and

VL is SEQ ID NO: 52.

In some embodiments, the antibody or antigen binding fragment thereof comprises a light chain variable region (VL) and/or a heavy chain variable region (VH), wherein:

VH is SEQ ID NO: 53,
and

VL is SEQ ID NO: 54.

In some embodiments, the antibody or antigen binding fragment thereof comprises a light chain variable region (VL) and/or a heavy chain variable region (VH), wherein:

VH is SEQ ID NO: 55,
and

VL is SEQ ID NO: 56.

In some embodiments, the lung cancer is non-small cell lung cancer (NSCLC). In some embodiments, the lung cancer is small cell lung cancer (SCLC).

In some aspects, disclosed herein is a method of producing an antibody or antigen binding fragment thereof, comprising cultivating or maintaining a host cell of under conditions to produce the antibody.

EXAMPLES

The following examples are set forth below to illustrate the antibodies, compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Therapeutic Antibodies and Methods for Treating Lung Cancer

Lung cancer is predicted to cause over a quarter of all cancer-related mortalities in 2019, according to recent estimations by the American Cancer Society. Non-small cell lung cancer (NSCLC) is the most common subtype of disease, comprising up to 85% of all diagnosed cases.

Despite advances in surgical resection, chemotherapy, and targeted therapeutics, current treatment regimens only confer a 5-year survival benefit for 60-70% of patients with phase I disease. Immunomodulatory therapy targeting exhausted T cells is a promising alternative for NSCLC patients, but challenges remain in making immunotherapies more universally effective as response rates are limited to 20% among patient cohorts. The clinical success of T-cell targeted therapy has galvanized the field to study other tumor-resident immune cell populations. Observations from these studies further reinforce the premise that immune populations other than T cells, such as tumor-resident macrophages and NK cells, play a role in tumor progression.

The role of B cells, another type of tumor-resident immune population, is less clear. These cells are present in higher frequencies in lung tumors compared to non-malignant lung tissue, and this differential frequency between malignant and non-malignant tissue suggests an active role in tumor immunosurveillance. Although not well characterized mechanistically, intratumoral B cells associate with clinical outcome in lung cancer patients. Studies examining immune cell gene signatures in lung cancer patients implicate B cells as positive prognostic indicators for patient survival. Furthermore, ectopic lymphoid structure formation in lung tumors is associated with a positive clinical benefit. Conversely, secretion of immunosuppressive cytokines by B cells and B-cell exhaustion phenotypes correlate with deleterious patient outcomes. Thus far, the major findings regarding tumor-infiltrating B (TIL-B) cells have relied on bulk B-cell gene transcripts or bulk sorting of B cells. However, detailed studies of TIL-B cells at the single cell level are lacking.

Such single-cell TIL-B studies are significant for the NSCLC field for several reasons, including: (i) They help define the functional role of TIL-B cells within the NSCLC tumor microenvironment; (ii) They provide for the identification of new antibody candidates as therapeutic and diagnostic tools; (iii) They can identify new tumor-associated antigens for use as a vaccine or therapeutic target.

A number of studies have established potential associations between the presence of TIL-B cells and clinical outcomes for a number of different types of cancers. Efforts on antibody identification using next-generation sequencing and antigen-specific B-cell sorting techniques have been successful in a variety of settings, including for some types of cancers.

The results described herein are innovative in a number of aspects that make it a significant leap from the current knowledge in the art. One important innovation of this project lies in the identification of NSCLC-specific B cells from tumor samples. Select B cells are produced as recombinant monoclonal antibodies (mAbs) and tested in various functional assays. These antibodies are important for use as new therapeutic and diagnostic tools. These efforts also identify new tumor-associated antigens for use in as a vaccine or therapeutic target. Next-generation sequencing (NGS) of the B-cell receptors (BCR) for a large number of patients provides an in-depth view of TIL-B repertoires in the context of NSCLC. A variety of techniques, including antigen-specific B-cell sorting, next-generation sequencing of antibody repertoires, and monoclonal antibody functional validation assays are used.

The B-cell repertoires in tumor samples from a cohort of NSCLC patients are characterized. Samples for NSCLC patients (samples include female and male patients; aged 60-80; diagnosed with adenocarcinoma) are analyzed.

Intratumoral B-cell signatures across a number of studies in NSCLC point to a tumor-reactive, antibody-mediated response. Tertiary lymphoid structures, which mimic the B-cell maturation process outside of secondary lymph nodes, have been noted to form in lung tumors, and have also been associated with a positive clinical benefit. Functional studies of cancer patient-derived B-cell supernatants display reactivity to canonical tumor-associated antigens, while recombinant antibodies derived from patient tumors demonstrate an affinity to intracellular proteins. Furthermore, human lung tumor engraftments in mice demonstrate the ability to produce tumor-reactive immunoglobulin. Systems-level analysis of intratumoral B-cell receptor sequences has identified clonally expanded B-cell lineages with extensive somatic hypermutation in repertoires from melanoma and gastric cancer; however, similar work has not been done in NSCLC. Despite evidence that B-cell proliferation, class-switch, and antibody secretion occur in the tumor, the antigen specificity of the TIL-B repertoire remains unclear.

Example 2. Identification of NSCLC-Specific B Cells Through Next-Generation Sequencing (NGS)

B cells were isolated from cryopreserved human lung cancer tissue and recovered B-cell receptor (BCR) sequences by paired heavy and light chain single cell RNA sequencing. From these experiments, clonally expanded B-cell populations and convergent BCR sequences shared between different patients were obtained. It was also demonstrated that recombinant antibodies derived from lung cancer patients bind cultured lung cancer cell lines in a dose-dependent manner. This data shows that tumor-resident B-cells secrete functional antibodies that may additionally be tumor-reactive. These novel antibodies not only serve as a source for therapeutic and diagnostic agents but also help inform vaccine design in lung cancer indications.

Paired heavy-light chain B-cell receptor (BCR) sequencing is performed for a set of tumor samples from individuals with NSCLC, typically generating on the order of thousands of unique BCR sequences per sample. Computational analysis is applied to the resulting sequence datasets, in order to identify putative tumor-specific B cells, by utilizing several different approaches, including the identification of clonally expanded B-cell lineages within each individual or of "public" B-cell lineages that are found in multiple individuals. Select B cells are produced as monoclonal antibodies and tested for antigen specificity in cultured NSCLC cell lines, as well as to autologous and heterologous patient tumor samples. Overall, this example identifies TIL-B cells that are tumor-specific, using criteria that are based on the properties of the B cell populations observed in the NGS experiments. While these efforts do not target a specific antigen, they led to the identification of novel antigen targets through antibody-antigen specificity screening.

B-Cell Isolation, Library Preparation, and NGS.

To ensure purity for library preparation, lung tumor single-cell suspensions are enriched for B cells by using fluorescence activated cell sorting (FACS) to negatively select for cells expressing a viability marker, CD3, CD14, and positively selecting for cells expressing CD19. This eliminates dead cells, T cells (CD3+), and monocytes (CD14+), respectively. CD19+B cells are then sorted and processed into cDNA libraries using the 10× Genomics single-cell 5' VDJ direct target enrichment workflow, for a target capture of 10,000 B cells per ⅛ 10× cassette. Library preparations are then sequenced on a NovaSeq sequencer at the VANTAGE sequencing core, with 150 base paired end reads at a target of at least 10,000 reads per cell. This approach results in the generation of a dataset of paired heavy-light chain BCR sequences for thousands of individual B cells per sample. Further discussion of materials and methods for identifying paired heavy-light chain BCR sequences can also be found in WO2020033164, which is herein incorporated by reference in its entirety.

Computational Analysis of NGS Data.

After sequencing, fastq files are processed using CellRanger software (10× Genomics, USA) and in-house scripts. Two strategies for identifying tumor-specific B cells from the NGS data are used:

(i) Identification of clonally expanded B-cell lineages within each sample. Within a sample, a B-cell (antibody) lineage is defined to contain a set of antibody sequences with identical V and J genes, and high CDR3 sequence identity for the heavy and light chains. Different levels of CDR3 sequence identity, including 100% (for completely identical CDR3 sequences), as well as lower cutoffs (e.g., 90% or 80%). This allows the identification of antibody lineage members with a small number of mutations within the CDR3 region, which is common in B-cell lineage development. TIL-B cells that are enriched within a tumor sample, are investigated as an indicator of tumor reactivity.

(ii) Identification of public B-cell lineages that are found in multiple individuals. The concept of public clonotypes is established for T cells. For B cells, because of the diversity of the antigen-recognition regions of the antibody sequence, the concept of antibody "publicness" is less clear. Yet, there are a number of examples in recent studies, that have shown that public antibodies exist in a variety of settings, including after infection/vaccination or auto-immunity and work on HIV-1 infection. See WO2019/143884.

Public B cells are identified that are found in multiple samples, as a potential indicator of tumor reactivity. Sequences from all samples are clustered simultaneously, requiring that all sequences within a given cluster must use the same heavy chain V/J and light chain V/J genes, and CDR3 sequences of high identity. Clusters that include sequences from multiple donors are defined as public antibody clusters. Different levels of CDR3 sequence identity are used.

Monoclonal Antibody (mAb) Production and Testing.

Based on the two analysis strategies described above, B cells are selected to produce and characterize as monoclonal antibodies.

Cloning and Production of mAbs

Selected antibody sequences are cloned into the expression vectors pFUSEss-CHIg-hG1 (heavy), pFUSE2ss-CLIg-hK (kappa light), and pFUSE2ss-CLIg-hL2 (lambda light). 293F cells are co-transfected with plasmids expressing matched pairs of heavy and light chain genes. Recombinant antibodies are purified on a protein A affinity column.

Binding to cell lines: Flow cytometry cell-binding assays are utilized to determine mAb binding to NSCLC cell lines (A549, PC9, and H23) as well as to control normal lung cell lines (16HBE, BEAS-2B, HBEC3-KT) and other non-cancer cell lines (HEK-293F). Adherent cultured cells are collected after treatment with TrypLE to promote dissociation from the plate. Cells are washed twice in DPBS+1% BSA. Cell reactivity is tested in both permeabilized and non-permeabilized conditions to detect extracellular and intracellular protein targets. 106 cells are then aliquoted into flow cytometry falcon tubes and stained with candidate patient-derived mAbs. Cells are washed twice in DPBS+1% BSA. Binding is detected by a secondary FITC anti-human Fc antibody. Samples are analyzed on a 4-laser Fortessa instrument using a 488 nm filter. Mean fluorescence intensity (MFI) is measured and analyzed in FlowJo.

Binding to Tumors

Immunohistochemistry is performed on formalin fixed paraffin embedded (FFPE) individual patient tumors as well as tissue microarrays, in order to establish mAb binding to autologous and heterologous tumors. These samples are prepared by the Translational Pathology Shared Resource at Vanderbilt. First, sections are blocked in 2.5% normal donkey serum (NDS) in PBS followed by incubation with 10 μg/mL mAb that are chimerized with a murine constant region. Bound mAb is detected by donkey anti-mouse conjugated to Cy5. Sections are further counterstained with Hoechst 33258 and then mounted with Prolong Antifade to protect from fluorophore photobleaching. Slides are visualized using a Nikon NiE microscope.

Antigen Identification

Multiple approaches are used for identifying mAb antigen targets. Western blot. Cultured cell lines are grown to confluence and harvested to create cell lysates. Briefly, cells are washed with DPBS and lysed by the addition of 50 mM Tris pH 8.0, 150 mM NaCl, 1% Triton X-100. Protease inhibitors are also added to prevent proteolysis during lysate collection. 30 µg of cell lysate is run on an SDS-PAGE gel, and then transferred to a nitrocellulose membrane. Blots are then incubated with candidate mAbs overnight, followed by an hour incubation of anti-human secondary-HRP conjugated antibody. Bound antibody is visualized by a chemiluminescent substrate and compared to a protein ladder standard.

Immunoprecipitation.

Monoclonal antibodies (mAbs) are conjugated to protein A magnetic beads and incubated with collected cell lysates. Antigen-protein interaction is disrupted by treatment with Laemmli denaturation buffer. Eluted proteins are run on an SDS-PAGE gel, and also transferred and blotted on nitrocellulose membrane to confirm protein pulldown. To ascertain the identity of precipitated proteins, bands are excised from an SDS-PAGE gel and sent for in-gel tryptic digestion and time-of-flight mass spectrometry peptide fingerprinting.

Antigen Microarrays.

mAbs are sent to PepperPrint (Heidelberg, Germany) for testing against 15,000 proteins spanning the human proteome. IgG is screened against a more focused microarray of 35,000 overlapping peptide sequences, corresponding to around 100 proteins associated with expression in lung cancers. Hemagglutinin and polio epitopes serve as positive controls in each assay.

Data analysis for protein reactivity is done using PepSlide Analyzer software, resulting in a panel of top hits for antigen specificity for each mAb.

Next-Generation Sequencing

Figure 2A:
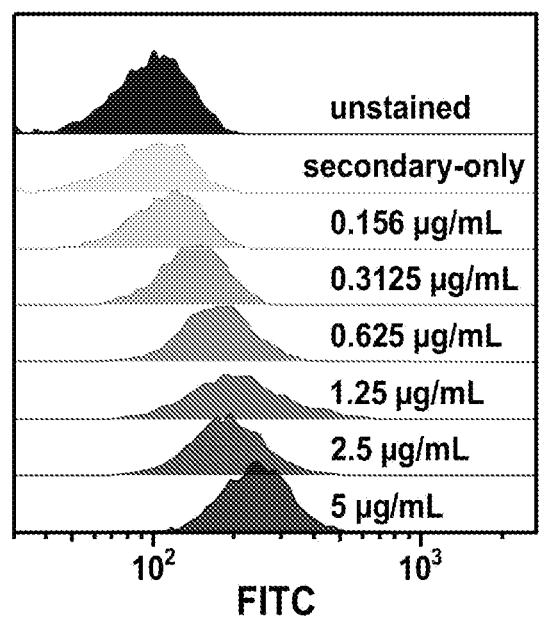
FIGS. 2A-2B shows mAb LTKK2 binds cultured adenocarcinoma cell line PC9. (A) FITC signal (x-axis) for different mAb concentrations (y-axis) is transformed into (B) mean fluorescence intensity (MFI) values (y-axis) plotted as a binding curve against the mAb concentration values (x-axis).
Figure 2B:
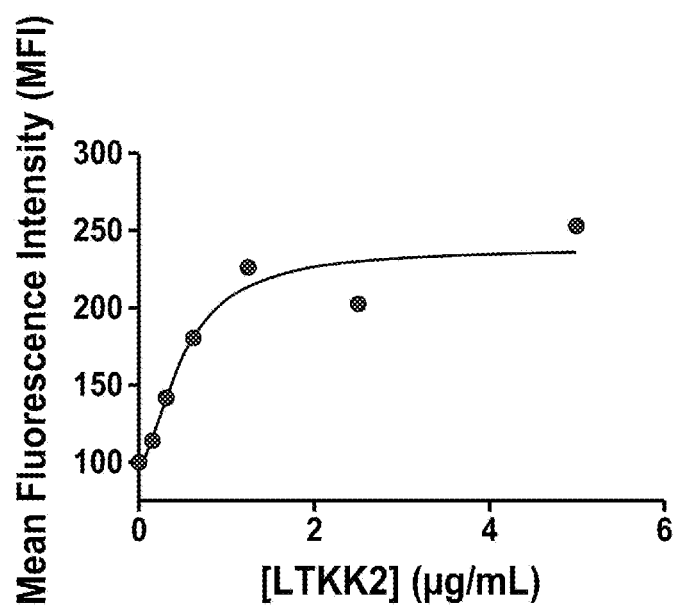

NGS analysis of the B-cell repertoire in an NSCLC tumor sample from a patient diagnosed with adenocarcinoma at a IIIA clinical stage is performed. Sequences for a total of 2,158 B cells with paired heavy-light chain information were clustered into lineages using a 100% cutoff for CDR3 identity, along with same V and J germline gene usage for both the heavy and light chains. A significant enrichment was observed for the top five most populated B-cell lineages in the NSCLC tumor sample (donor 1), compared to a control healthy PBMC sample (P=0.0079, Mann-Whitney test) (FIG. 1). In particular, the top two lineages in the NSCLC sample each comprised >3% of all B-cell sequences in the sample. This was in stark contrast to CD19+ cells from a healthy donor's PBMCs (public data from 10× Genomics), in which the most abundant lineage represented only 0.04% of the cell population (FIG. 1). Given these results, a representative B cell was selected from three of the top lineages for mAb production and characterization (Table 1). mAb LTKK2 (corresponding to one of the top two lineages) showed binding to PC9, a lung adenocarcinoma cell line (FIG. 2).

TABLE 1

Representative mAbs from three abundant B-cell lineages in donor 1. For each antibody heavy (IGH) and light (kappa, IGK; lambda, IGL) chain, shown are % nucleotide identity to germline V gene, and amino acid CDR3 length and sequence. Sequences in Table: ARDPYNWNANYYIDV (SEQ ID NO: 21); LQHNSYPYT (SEQ ID NO: 24); ARDAGSDAFDI (SEQ ID NO: 27); QQSYSTPAT (SEQ ID NO: 30); GRLTYHYDSSGFVSTVGNALDV (SEQ ID NO: 39); HQYGSSPQT (SEQ ID NO: 42).

| Name  | Chain | V Gene  | V identity % | CDR 3 length | CDR 3 sequence          |
|-------|-------|---------|--------------|--------------|-------------------------|
| LTKK1 | IGH   | 4-61*02 | 96.91        | 15           | ARDPYNWNANYYIDV         |
|       | IGL   | 1-17    | 97.85        | 9            | LQHNSYFYT               |
| LTKK2 | IGH   | 3-33*01 | 97.92        | 11           | ARDAGSDAFDI             |
|       | IGK   | 1D-39   | 98.92        | 9            | QQSYSTPAT               |
| LTKK3 | IGH   | 1-69*01 | 89.93        | 21           | GRLTYHYDSSGFVSTVGNALDV  |
|       | IGL   | 3-20    | 94.68        | 9            | HQYGSSPQT               |

In addition to the strategy of identifying expanded B-cell lineages, experiments were performed for the identification of public antibodies found in multiple NSCLC tumor samples.

Figure 3A:
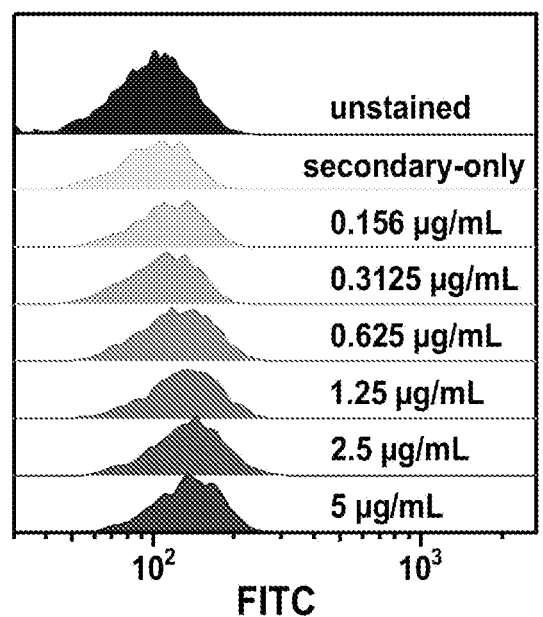
FIGS. 3A-3B shows mAb LTH_3.1.1 bound to cultured adenocarcinoma cell line PC9 in a dose-dependent manner. (A) FITC signal (x-axis) for different mAb concentrations (y-axis) is transformed into (B) mean fluorescence intensity (MFI) values (y-axis) plotted as a binding curve against the mAb concentration values (x-axis).
Figure 3B:
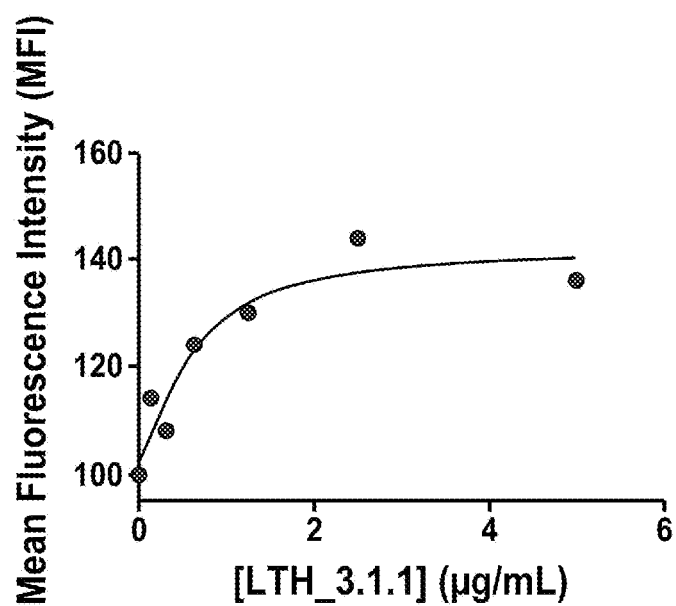

To that end, NGS analysis of the B-cell repertoires of two additional NSCLC tumor samples was performed, and identified public B-cell clusters that contained BCR sequences from multiple individuals, using the approach described above. A public cluster shared between two donors was identified (Table 2). One of these antibodies, LTH_3.1.1, showed binding to the PC9 cell line (FIG. 3).

TABLE 2

Sequence features for mAbs from an antibody cluster shared between two donors. Sequences in Table: ARVQLLADDVLDI (SEQ ID NO: 33); QQYGRSPLT (SEQ ID NO: 36); ARVQLADDVLNI (SEQ ID NO: 57); QQYGSSPLT (SEQ ID NO: 58).

| Name      | Chain | V Gene  | V identity (%) | CDR3 length | CDR3 sequence  | Donor |
|-----------|-------|---------|----------------|-------------|----------------|-------|
| LTH_3.1.1 | IGH   | 3-74*03 | 90.722         | 13          | ARVQLLADDVLDI  | 1     |
|           | IGK   | 3020*01 | 93.728         | 9           | QQYGRSPLT      |       |
| LTH_3.2.1 | IGH   | 3-74*03 | 95.254         | 13          | ARVQVLADDVLNI  | 2     |
|           | IGK   | 3-20*01 | 94.077         | 9           | QQYGSSPLT      |       |

Tumor-specific antibodies are identified in the context of NSCLC. The antibodies show potent binding to heterologous tumors (and to lung cancer cell lines but not to healthy lung or other cell lines), and target extracellular antigens.

Antibodies that do not bind heterologous tumors or cell lines, but that bind autologous tumor, coindicate a patient-specific response; the frequency of patient-specific vs. cross-reactive antibodies in different samples is determined. In addition to the BCR sequences, the platform allows for simultaneously obtaining single-cell RNA-seq data that provides additional information about the B-cell gene expression profiles (paired with the respective BCR sequences).

Further, the NGS sequences cover the entire variable domains for both heavy and light chains, and have sufficient coverage of the constant regions for determination of isotype, thus allowing isotype prevalence determination within the NSCLC tumor environment.

Example 3. Identification of NSCLC-Specific B Cells Through Antigen-Specific B-Cell Sorting Antigen-specific B-cell sorting is performed for a set of tumor samples from individuals with NSCLC. Antigens are used that are known to play a role in lung cancer. Specifically, Mucin 1 (MUC1), vascular endothelial growth factor (VEGF), and angiopoietin-2 (Ang-2) are analyzed.

MUC1 is a highly overexpressed protein in NSCLC implicated in uncontrolled cell proliferation, and its expression is an adverse predictor for patient survival. The observation of MUC1 antibody titer and its association with improved patient survival in the clinic suggests that cancer patients may mount their own beneficial immune response. This evidence supports the claim that MUC1-reactive antibodies isolated from human patients can serve as potent therapeutic molecules and be tumor-specific. MUC1 is highly glycosylated in normal tissue, but its expression in cancer tissue favors aglycosylated variants, initiating an immunogenic response against masked epitopes in healthy tissue. In the antigen-specific sort, an un-glycosylated peptide is used which comprises a solvent-exposed portion of the extracellular domain.

VEGF, an established therapeutic target, initiates the sprouting of new blood vessels and is implicated as a primary driver of tumor progression in lung cancer. While less is known about the function of Ang-2 in lung cancer, its expression is elevated in malignant tissue compared to normal tissue and is associated with poor clinical outcomes. While these two proteins are not tumor-specific in function, overexpression of VEGF or Ang-2 may trigger the proliferation of autoreactive B cells.

From the sorting experiments, a set of antigen-specific B cells is produced as monoclonal antibodies and tested for antigen specificity. This example identifies tumor-resident B cells that target established tumor-associated antigens.

Antigen-specific B-cell sorting.

MUC1 is ordered as a peptide biotinylated at the C terminus (GenScript). Avi-tagged VEGF and Ang-2 recombinant DNA constructs are transfected in HEK-293F cells, grown for 4 days and purified over Nickel chromatography resin. Briefly, cell supernatant is applied to nickel charged chromatography resin, and his-tagged protein is eluted with PBS+500 mM imidazole. Eluate is buffer exchanged into PBS, concentrated on 10K MWCO filters, and purified further by size-exclusion chromatography using a Superose 6B 10/300 GL column. Proteins are biotinylated using the BirA ligase kit (Avidity). Antigens are fluorescently labeled by adding fluorescent streptavidin conjugates at a 1:4 molar stoichiometric ratio. Fluorescent streptavidin is added in 0.2× increments every 20 minutes on a rotator at 4 C. FACS sorting is used to negatively select for cells expressing a viability marker, CD3, and CD14; and positively select for cells expressing CD19 and positive for any of the fluorescently-labeled antigens. Cells are single-cell sorted in PCR plates containing lysis buffer, and the BCRs are amplified out of each cell, and cloned into a mammalian expression vector for recombinant production in 293F cells. BCR sequences are amplified out of single cells using a nested PCR approach.

Monoclonal Antibody (mAb) Production and Testing.

Antibodies are identified from antigen-specific B cells. The production and characterization of mAbs is performed as described above, with the addition of confirming binding to the sorting antigens.

Briefly, for ELISA binding, 2 µg/mL of an antigen is plated overnight on Nunc Immuno plates followed by blocking, and incubation with threefold serial dilutions of primary antibody starting at 20 µg/mL.

Binding is detected by HRP-conjugated anti-human IgG secondary. Data is reported as absorbance at 450 nm. To compute antibody-antigen affinities, biolayer interferometry is performed on an Octet Red 96 instrument available through the Vanderbilt Antibody and Protein Resource (VAPR) core.

Figure 4A:
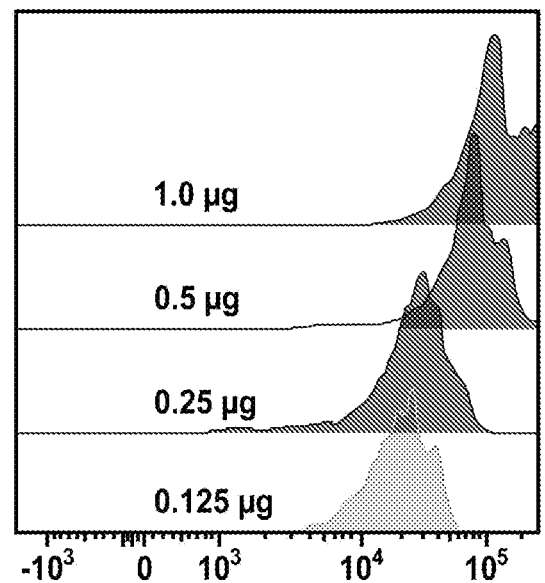
FIGS. 4A-4B. Fluorescent labeling of Ang-2. (A) Ang-2 bound anti-Ang2 protein-A compensation beads, but (B) no shift in signal was observed on IgG control compensation beads compared to unstained beads.
Figure 4B:
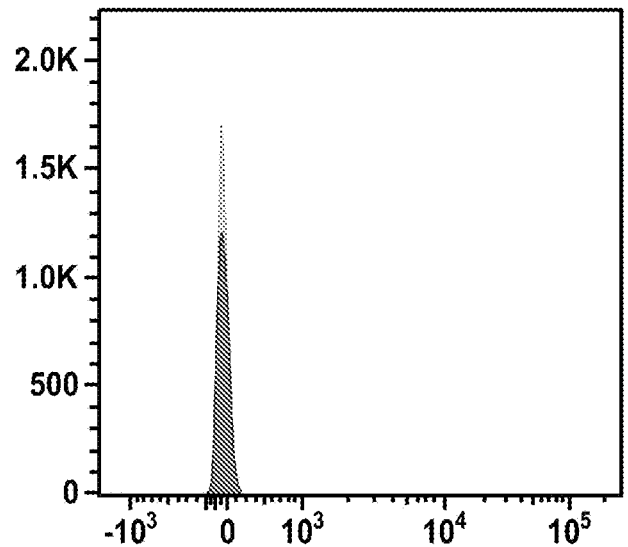

Fluorescently labeled recombinant Ang-2 was produced, and reactivity was confirmed with an anti-Ang2 antibody (FIG. 4), and is used in antigen-specific B-cell sorting experiments.

Antibodies specific to the set of target antigens is identified. Other lung cancer specific antigens, such as Insulin growth factor binding protein 2 (IGFBP2) are also used. Auto-antibody titer against IGFBP-2 is elevated compared to healthy controls, increases with tumor stage, and serves as a diagnostic biomarker, and evidence of its pro-tumorigenic role in lung cancer show that inhibition can confer a therapeutic benefit. Other targets include the cancer-testis antigens NY-ESO-1 and XAGE-1b that have been shown to stimulate auto-antibody responses in lung cancer patients.

By utilizing two different approaches—the antigen-agnostic approach and the antigen-specific approach, these examples provide identification of tumor-specific antibodies in the context of NSCLC. Therapeutic antibodies can specifically recognize lung cancer cell lines and autologous/heterologous tumors, as well their target antigens, and are used for treating lung cancers.

Example 4. Additional Antibody Analysis

Figure 5A:
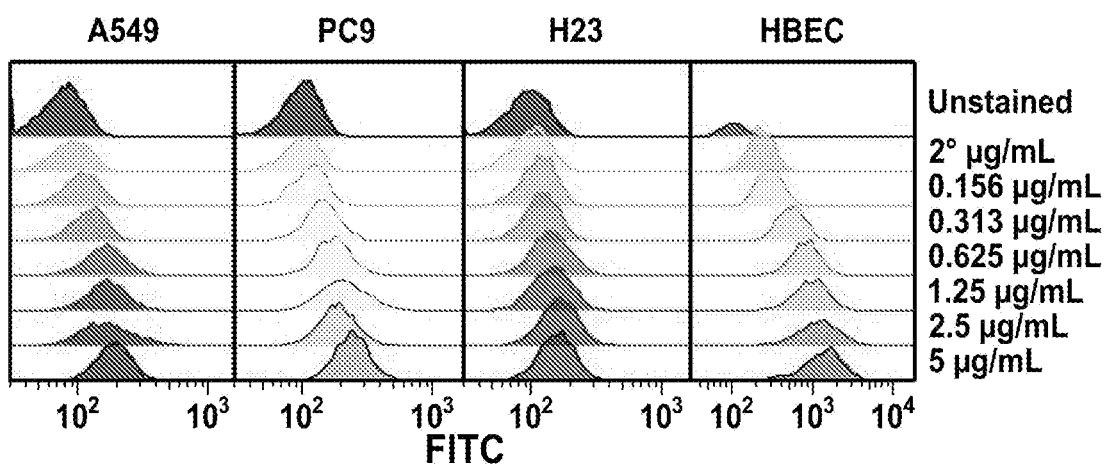
FIGS. 5A-5C shows plots from a flow-cytometry binding assay for antibody LTKK2.
Figure 5B:
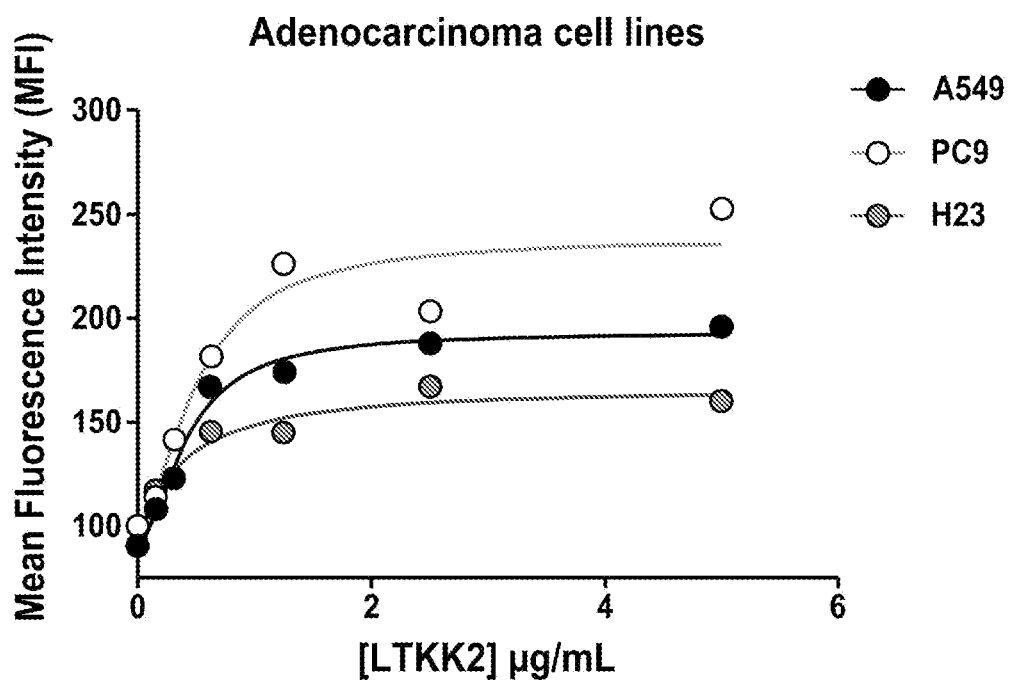
Figure 5C:
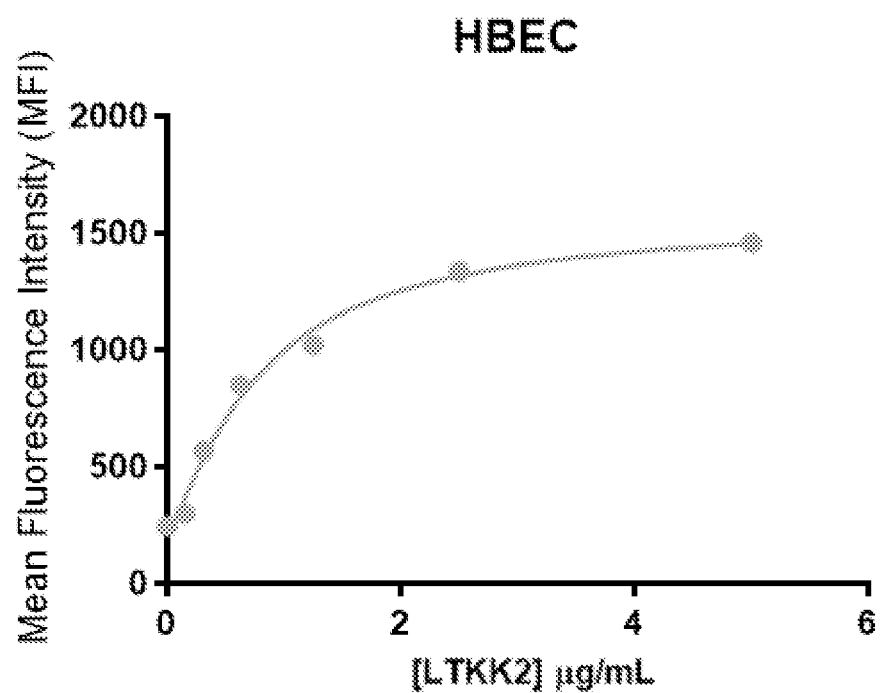

This example shows that patient-derived antibodies can bind cancer cell lines suggesting they may be tumor specific. Shown in FIG. 5 is a binding assay of patient-derived antibody showing a dose dependent binding response to the lung adenocarcinoma cell line A549. This data is from the flow cytometry-based assay where antibodies are incubated with cells and detected with an anti-human Fc FITC secondary.

Data shows a shared antibody repertoire between cancer patients. When antibody sequences were compares between different patients, similar sequences were identified. Shown below (Table 3) are example amino acid sequences of the antibody CDR3 region with 100, 80, and 70% sequence identity.

TABLE 3

Amino acid sequence of the antibody CDR3 region with 100, 80, and 70% sequence identity.

| AA Sequence Identity | Sample | CDRH3 AA Sequence | % Identity to Germline |
|---|---|---|---|
| 100% | 1 | ARPMTTVTPKAFDI (SEQ ID NO: 59) | 85.9 |
|  | 2 | ARPMTTVTPKAFDI (SEQ ID NO: 59) | 93.9 |
| 80% | 2 | ARVQLLADDVLDI (SEQ ID NO: 60) | 86.5 |
|  | 1 | ARVQVLADDVLNI (SEQ ID NO: 61) | 92.9 |
| 70% | 3 | ARDPAGDAFDI (SEQ ID NO: 62) | 94.9 |
|  | 1 | ARDPAWGAYDI (SEQ ID NO: 63) | 86.7 |

Example 5. Monoclonal Antibody (D5) Characterization

A B cell (and monoclonal antibody D5) was identified with reactivity to vascular endothelial growth factor (VEGF) from a human lung tumor sample. The B cell receptor sequence was isolated from this cell by RT-PCR and V(D)J targeted PCR. The resulting heavy and light chain sequences were expressed as a recombinant, soluble antibody and binding reactivity was confirmed by ELISA.

Figures 6A, 6B, 6C, 6D:
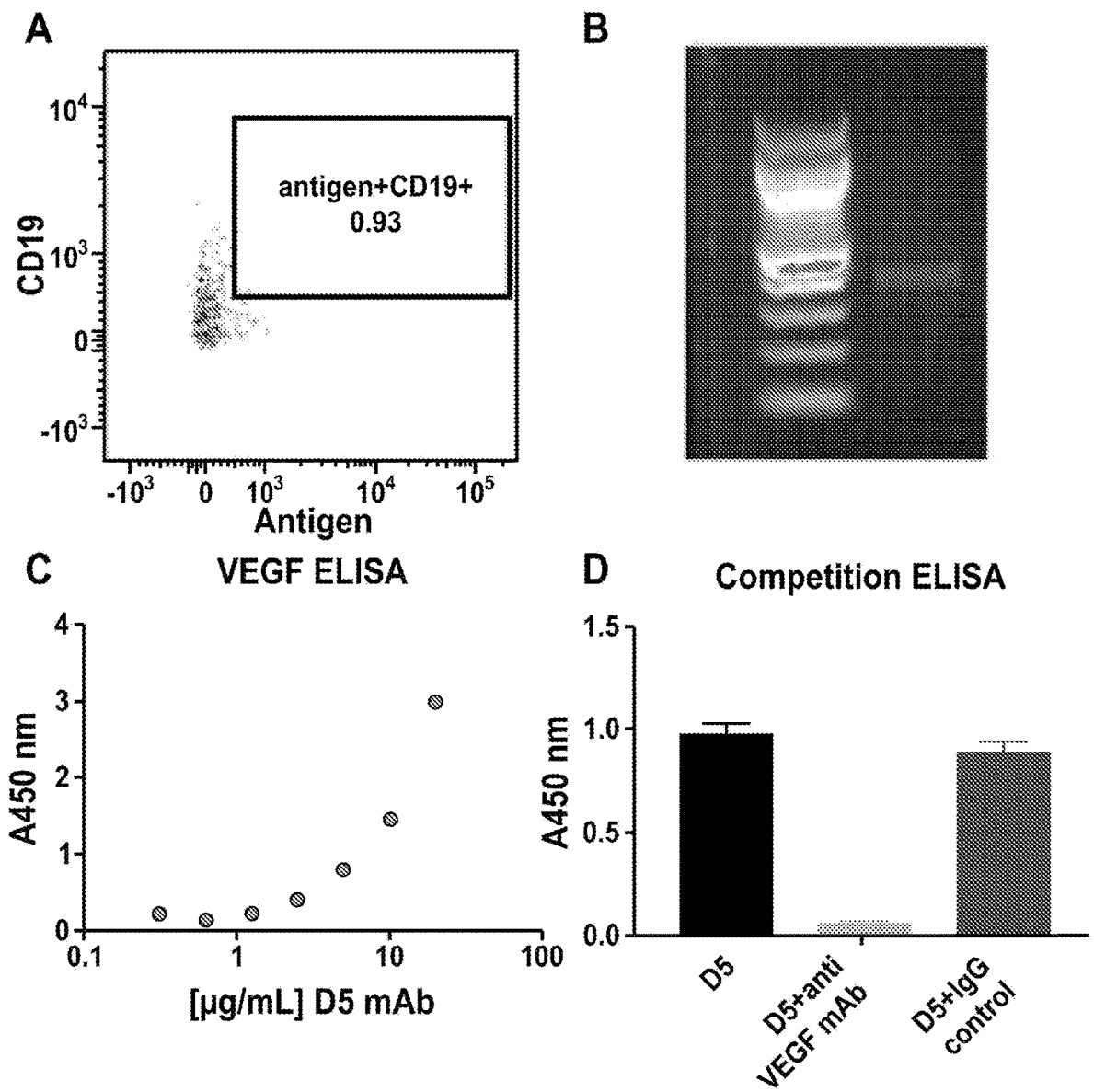
FIGS. 6A-6D shows the characterization of monoclonal antibody D5.

Additionally, this antibody D5 competes with the FDA-approved anti-VEGF antibody, Bevacizumab (AVASTIN®) (FIG. 6). This is the first demonstration of a monoclonal specificity derived from a tumor-infiltrating B cell population. This observation shows B cells secreting immunoglobulin or participating in antigen presentation, and thus providing a more important role in the context of the tumor microenvironment. This suggests a mechanism of VEGF neutralization and angiogenic cascade inhibition. These findings identify a new TIL-B function in B-cell phenotypes in lung cancer. The antibody sequences for D5 are provided in Table 4 and Table 5.

Sequences

TABLE 4

CDR Sequences

| Antibody (HC or LC) | CDR1 | CDR2 | CDR3 |
|---|---|---|---|
| D5 HC | GFTVSSNY (SEQ ID NO: 1) | IYTGGGT (SEQ ID NO: 2) | AREAPFTAALLYY (SEQ ID NO: 3) |
| D5 LC | SSDVG (SEQ ID NO: 4) | EVT (SEQ ID NO: 5) | SSYAGNNNRVV (SEQ ID NO: 6) |
| B12 HC | GYIFEAYG (SEQ ID NO: 7) | ISVFNGDR (SEQ ID NO: 8) | ATGAELLSAFGV (SEQ ID NO: 9) |
| B12 LC | TSNIGAGYE (SEQ ID NO: 10) | GNT (SEQ ID NO: 11) | QSYDSSRGGFWV (SEQ ID NO: 12) |
| A7 HC | GFAFSTYV (SEQ ID NO: 13) | ISHEGSDK (SEQ ID NO: 14) | AKEGPRDYYYYGWDV (SEQ ID NO: 15) |
| A7 LC | SSDVGAYNY (SEQ ID NO: 16) | EVK (SEQ ID NO: 17) | SSYVRSGTRV (SEQ ID NO: 18) |
| LTKK1 HC | GGSISSGSYY (SEQ ID NO: 19) | IYMSGTT (SEQ ID NO: 20) | ARDPYNWNANYYIDV (SEQ ID NO: 21) |
| LTKK1 LC | QGIRND (SEQ ID NO: 22) | AAS (SEQ ID NO: 23) | LQHNSYPYT (SEQ ID NO: 24) |
| LTKK2 HC | GFTFSTYV (SEQ ID NO: 25) | IWYDGSNK (SEQ ID NO: 26) | ARDAGSDAFDI (SEQ ID NO: 27) |
| LTKK2 LC | QSISSY (SEQ ID NO: 28) | AAS (SEQ ID NO: 29) | QQSYSTPAT (SEQ ID NO: 30) |
| LTH_3.1.1 HC | GFPFSNYW (SEQ ID NO: 31) | ISGDGSST (SEQ ID NO: 32) | ARVQLLADDVLDI (SEQ ID NO: 33) |
| LTH_3.1.1 LC | QSVYANH (SEQ ID NO: 34) | GAS (SEQ ID NO: 35) | QQYGRSPLT (SEQ ID NO: 36) |
| LTKK3 HC | GGIVHSYS (SEQ ID NO: 37) | VVPVFDTR (SEQ ID NO: 38) | GRLTYHDSSGFVSTVGNALDV (SEQ ID NO: 39) |
| LTKK3 LC | QSVTNIY (SEQ ID NO: 40) | GAS (SEQ ID NO: 41) | HQYGSSPQT (SEQ ID NO: 42) |

TABLE 5

Heavy Chain and Light Chain Variable Region Sequences

| Antibody (HC or LC) | Heavy Chain Variable Region or Light Chain Variable Region Sequence |
|---|---|
| D5 HC | EVQLVESGGGLIQPGGSLRLSCAASGFTVSSNYMSWVRQAPGKGLEWVSV IYTGGGTYYADSVKGRFTISRDNSQNTLYLQMNSLRAEDTAVYYCAREAP FTAALYYWGQGTLVTVSS (SEQ ID NO: 43) |
| D5 LC | QSVLTQPPSASGSPGQSVTISCTGTSSDVGGYNSVSWYQQHPGKAPKLMIY EVTIRPSGVPDRFSGSKSGNTASLTVSGLQAEDEADYYCSSYAGNNNRVVF GGGTKLTVL (SEQ ID NO: 44) |
| B12 HC | QVQLVQSGPEVKKPGASVKVSCKASGYIFEAYGINWARQAPGQGLEWLG WISVFNGDRQYAQNFQGRVTMTTDKSSNTAYLELSSLRSGDTAVYYCAT GAELLSAFGVWGQGTTVTVSS (SEQ ID NO: 45) |
| B12 LC | QSVLTQPPSVSGAPGQRVTISCTGSTSNIGAGYEVNWYQQLPGRAPKLLIS GNTDRPSGVPDRFSGSKSGTSASLAITGLRAEDEADYYCQSYDSSRGGFW VFGGGTKVTVL (SEQ ID NO: 46) |
| A7 HC | EVQLVESGGGVVQPGRSLRLSCAASGFAFSTYVMHWVRQAPGKGLEWV AAISHEGSDKYYVDSVKGRFTISRDNSKNTLHLQMNSLRIEDTAVYYCAK EGPRDYYYGWDVWGQGTTVIVSS (SEQ ID NO: 47) |
| A7 LC | QXVLTQPASVSGSPGQSITISCTGTSSDVGAYNYVSWYQQYPGKAPTLLIF EVKYRPSGVPNRFSGSKSGNTASLTISGLRSEDEADYYCSSYVRSGTRVFG GGTKVTVL (SEQ ID NO: 48) |
| LTKK1 HC | QVQLQESGPGLVKPSQTLSLTCNVSGGSISSGSYWSWIRQPAGKGLEWIG RIYMSGTTNYNPSLKSRVTISLDTSKNQFSLRLRSVTAADTAVYYCARDPY NWNANYYIDVWGKGTTVTVSS (SEQ ID NO: 49) |
| LTKK1 LC | DIQMTQSPSSLSASVGDRVTITCRASQSISSYLNWYQQKPGKAPKLLIYAAS SLQSGVPSRFSGSGSGTDFTLTISSLQPKDFATYYCQQSYSTPATFGGGTKV EIK (SEQ ID NO: 50) |
| LTKK2 HC | QVQLVESGGGVVQPGRSLRLSCAASGFTFSTYVMHWVRQAPGKGLEWV AVIWYDGSNKYYTDSVKGRFTISRDNSKNTLYLEMNSLRAEDTAVYYCA RDAGSDAFDIWGQGTMVTVSS (SEQ ID NO: 51) |
| LTKK2 LC | DIQMTQSPSSLSASVGDRVTITCRASQSISSYLNWYQQKPGKAPKLLIYAAS SLQSGVPSRFSGSGSGTDFTLTISSLQPKDFATYYCQQSYSTPATFGGGTKV EIK (SEQ ID NO: 52) |
| LTH_3.1.1 HC | QLVESGGASVQPGGSLRLSCAASGFPFSNWIHWVRQAPGKGPEWVSRIS GDGSSTSYADSVKGRFTISRDNARNMLYLQMNSLRVEDTALYYCARVQL LADDVLDIWGQGTMVTVSS (SEQ ID NO: 53) |
| LTH_3.1.1 LC | EIVLTQSPGTLSLSPGERATLSCRASQSVYANHIAWYQQKPGQAPRRLFFG ASIRAYGIPDRFSGSGSGTDFTLTISSLEPEDFAVYYCQQYGRSPLTFGGGT KVEMK (SEQ ID NO: 54) |
| LTKK3 HC | QVQLVQSGAEMKKPGSSVKVSCKASGGIVHSYSLSWVRQAPGQGLEWVG GVVPVFDTRKYAQKFQGRVTITADESTSTTYMELSSLRSEDTAVYYCGRL TYHYDSSGFVSTVGNALDVWGQGTMVIVSS (SEQ ID NO: 55) |
| LTKK3 LC | EIVLMQSPGTLSLSPGERATLSCRASQSVTNIYLAWYQQKPGQAPRLLIYG ASRRATGIPDRFSGSGSGTDFTLTINRLEPEDFGVYFCHQYGSSPQTFGQGT KVEIK (SEQ ID NO: 56) |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A recombinant antibody, wherein the antibody comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein the recombinant antibody comprises:

CDRH1 is GFTVSSNY, (SEQ ID NO: 1)

CDRH2 is IYTGGGT, (SEQ ID NO: 2)

CDRH3 is AREAPFTAALYY, (SEQ ID NO: 3)

CDRL1 is SSDVG, (SEQ ID NO: 4)

CDRL2 is EVT, and (SEQ ID NO: 5)

CDRL3 is SSYAGNNNRVV; (SEQ ID NO: 6)

CDRH1 is GYIFEAYG, (SEQ ID NO: 7)

CDRH2 is ISVFNGDR, (SEQ ID NO: 8)

CDRH3 is ATGAELLSAFGV, (SEQ ID NO: 9)

CDRL1 is TSNIGAGYE, (SEQ ID NO: 10)

CDRL2 is GNT, and (SEQ ID NO: 11)

CDRL3 is QSYDSSRGGFWV; (SEQ ID NO: 12)

CDRH1 is GFAFSTYV, (SEQ ID NO: 13)

CDRH2 is ISHEGSDK, (SEQ ID NO: 14)

CDRH3 is AKEGPRDYYYYGWDV, (SEQ ID NO: 15)

-continued

CDRL1 is SSDVGAYNY, (SEQ ID NO: 16)

CDRL2 is EVK, (SEQ ID NO: 17)
and

CDRL3 is SSYVRSGTRV; (SEQ ID NO: 18)

CDRH1 is GGSISSGSYY, (SEQ ID NO: 19)

CDRH2 is IYMSGTT, (SEQ ID NO: 20)

CDRH3 is ARDPYNWNANYYIDV, (SEQ ID NO: 21)

CDRL1 is QGIRND, (SEQ ID NO: 22)

CDRL2 is AAS, (SEQ ID NO: 23)
and

CDRL3 is LQHNSYPYT; (SEQ ID NO: 24)

CDRH1 is GFTFSTYV, (SEQ ID NO: 25)

CDRH2 is IWYDGSNK, (SEQ ID NO: 26)

CDRH3 is ARDAGSDAFDI, (SEQ ID NO: 27)

CDRL1 is QSISSY, (SEQ ID NO: 28)

CDRL2 is AAS, (SEQ ID NO: 29)
and

CDRL3 is QQSYSTPAT; (SEQ ID NO: 30)

CDRH1 is GFPFSNYW, (SEQ ID NO: 31)

CDRH2 is ISGDGSST, (SEQ ID NO: 32)

CDRH3 is ARVQLLADDVLDI, (SEQ ID NO: 33)

CDRL1 is QSVYANH, (SEQ ID NO: 34)

CDRL2 is GAS, (SEQ ID NO: 35)
and

CDRL3 is QQYGRSPLT; (SEQ ID NO: 36)

CDRH1 is GGIVHSYS, (SEQ ID NO: 37)

CDRH2 is VVPVFDTR, (SEQ ID NO: 38)

-continued

CDRH3 is GRLTYHDSSGFVSTVGNALDV, (SEQ ID NO: 39)

CDRL1 is QSVTNIY, (SEQ ID NO: 40)

CDRL2 is GAS, (SEQ ID NO: 41)
and

CDRL3 is HQYGSSPQT. (SEQ ID NO: 42)

2. The recombinant antibody of claim 1, wherein the antibody comprises a light chain variable region (VL) that comprises a light chain complementarity determining region (CDRL) 1, CDRL2, and CDRL3 and a heavy chain variable region (VH) that comprises a heavy chain complementarity determining region (CDRH) 1, CDRH2, and CDRH3, wherein:

CDRH1 is GFTVSSNY, (SEQ ID NO: 1)

CDRH2 is IYTGGGT, (SEQ ID NO: 2)

CDRH3 is AREAPFTAALYY, (SEQ ID NO: 3)

CDRL1 is SSDVG, (SEQ ID NO: 4)

CDRL2 is EVT, and (SEQ ID NO: 5)

CDRL3 is SSYAGNNNRVV. (SEQ ID NO: 6)

3. The recombinant antibody of claim 1, wherein the antibody comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

CDRH1 is GYIFEAYG, (SEQ ID NO: 7)

CDRH2 is ISVFNGDR, (SEQ ID NO: 8)

CDRH3 is ATGAELLSAFGV, (SEQ ID NO: 9)

CDRL1 is TSNIGAGYE, (SEQ ID NO: 10)

CDRL2 is GNT, and (SEQ ID NO: 11)

CDRL3 is QSYDSSRGGFWV. (SEQ ID NO: 12)

4. The recombinant antibody of claim 1, wherein the antibody comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

```
                                 (SEQ ID NO: 13)
CDRH1 is GFAFSTYV, (SEQ ID NO: 14)
CDRH2 is ISHEGSDK, (SEQ ID NO: 15)
CDRH3 is AKEGPRDYYYGWDV, (SEQ ID NO: 16)
CDRL1 is SSDVGAYNY, (SEQ ID NO: 17)
CDRL2 is EVK, and (SEQ ID NO: 18)
CDRL3 is SSYVRSGTRV.
```

5. The recombinant antibody of claim 1, wherein the antibody comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

```
                                 (SEQ ID NO: 19)
CDRH1 is GGSISSGSYY, (SEQ ID NO: 20)
CDRH2 is IYMSGTT, (SEQ ID NO: 21)
CDRH3 is ARDPYNWNANYYIDV, (SEQ ID NO: 22)
CDRL1 is QGIRND, (SEQ ID NO: 23)
CDRL2 is AAS, and (SEQ ID NO: 24)
CDRL3 is LOHNSYPYT.
```

6. The recombinant antibody of claim 1, wherein the antibody comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

```
                                 (SEQ ID NO: 25)
CDRH1 is GFTFSTYV, (SEQ ID NO: 26)
CDRH2 is IWYDGSNK, (SEQ ID NO: 27)
CDRH3 is ARDAGSDAFDI, (SEQ ID NO: 28)
CDRL1 is QSISSY,
```

-continued
```
                                 (SEQ ID NO: 29)
CDRL2 is AAS, and (SEQ ID NO: 30)
CDRL3 is QQSYSTPAT.
```

7. The recombinant antibody of claim 1, wherein the antibody comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

```
                                 (SEQ ID NO: 31)
CDRH1 is GFPFSNYW, (SEQ ID NO: 32)
CDRH2 is ISGDGSST, (SEQ ID NO: 33)
CDRH3 is ARVQLLADDVLDI, (SEQ ID NO: 34)
CDRL1 is QSVYANH, (SEQ ID NO: 35)
CDRL2 is GAS, and (SEQ ID NO: 36)
CDRL3 is QQYGRSPLT.
```

8. The recombinant antibody of claim 1, wherein the antibody comprises a light chain variable region (VL) that comprises a light chain complementarity determining region (CDRL)1, CDRL2, and CDRL3 and a heavy chain variable region (VH) that comprises a heavy chain complementarity determining region (CDRH)1, CDRH2, and CDRH3, wherein:

```
                                 (SEQ ID NO: 37)
CDRH1 is GGIVHSYS, (SEQ ID NO: 38)
CDRH2 is VVPVFDTR, (SEQ ID NO: 39)
CDRH3 is GRLTYHYDSSGFVSTVGNALDV, (SEQ ID NO: 40)
CDRL1 is QSVTNIY, (SEQ ID NO: 41)
CDRL2 is GAS, and (SEQ ID NO: 42)
CDRL3 is HQYGSSPQT.
```

9. A method of treating lung cancer, comprising administering to a subject in need thereof a therapeutically effective amount of the recombinant antibody of claim 1.

10. The method of claim 9, where the lung cancer is non-small cell lung cancer (NSCLC).

\* \* \* \* \*